United States Patent
Kitano et al.

(10) Patent No.: US 11,655,273 B2
(45) Date of Patent: May 23, 2023

(54) SUBSTRATES COATED WITH SELECTIVE CELL SEPARATION OR CELL CULTURE POLYMERS

(71) Applicants: NATIONAL UNIVERSITY CORPORATION UNIVERSITY OF TOYAMA, Toyama (JP); NISSAN CHEMICAL CORPORATION, Tokyo (JP)

(72) Inventors: Hiromi Kitano, Toyama (JP); Tadashi Nakaji, Toyama (JP); Yuki Usui, Toyama (JP); Taito Nishino, Shiraoka (JP); Takahiro Kishioka, Toyama (JP)

(73) Assignees: NATIONAL UNIVERSITY CORPORATION UNIVERSITY OF TOYAMA, Toyama (JP); NISSAN CHEMICAL CORPORATION, Tokyo (JP)

(*) Notice: Subject to any disclaimer, the term of this patent is extended or adjusted under 35 U.S.C. 154(b) by 617 days.

(21) Appl. No.: 16/629,494

(22) PCT Filed: Jul. 9, 2018

(86) PCT No.: PCT/JP2018/025820
§ 371 (c)(1),
(2) Date: Jan. 8, 2020

(87) PCT Pub. No.: WO2019/013148
PCT Pub. Date: Jan. 17, 2019

(65) Prior Publication Data
US 2021/0130788 A1    May 6, 2021

(30) Foreign Application Priority Data
Jul. 11, 2017 (JP) .............................. JP2017-135585

(51) Int. Cl.
| | | |
|---|---|---|
| *C12N 5/07* | (2010.01) | |
| *C08G 61/04* | (2006.01) | |
| *C07K 7/62* | (2006.01) | |
| *C08F 220/36* | (2006.01) | |
| *B01J 20/32* | (2006.01) | |
| *C08F 220/40* | (2006.01) | |
| *C09D 133/10* | (2006.01) | |
| *C09D 133/14* | (2006.01) | |
| *C12M 1/00* | (2006.01) | |
| *C12N 5/0775* | (2010.01) | |

(52) U.S. Cl.
CPC ............ *C07K 7/62* (2013.01); *B01J 20/3204* (2013.01); *B01J 20/327* (2013.01); *B01J 20/3274* (2013.01); *B01J 20/3285* (2013.01); *C08F 220/365* (2020.02); *C08F 220/40* (2013.01); *C09D 133/10* (2013.01); *C09D 133/14* (2013.01); *C12M 23/20* (2013.01); *C12N 5/0663* (2013.01); *C12N 2533/30* (2013.01)

(58) Field of Classification Search
CPC ............... B01J 20/3285; B01J 20/3274; B01J 20/3272; B01J 20/3204; B01J 20/327; C09D 133/10; C09D 133/14; C07K 7/62; C12N 5/0663; C12N 2533/30; C08F 220/365; C08F 220/40; C08F 220/387; C08F 220/085
USPC ...................... 435/372, 366, 363, 325; 520/1
See application file for complete search history.

(56) References Cited

U.S. PATENT DOCUMENTS

| | | | |
|---|---|---|---|
| 6,017,719 A | 1/2000 | Tseng-Law et al. | |
| 2003/0119070 A1 | 6/2003 | Schaeffer et al. | |
| 2003/0219445 A1 | 11/2003 | Schaeffer et al. | |
| 2008/0175758 A1 | 7/2008 | Matsumoto et al. | |
| 2015/0267159 A1 | 9/2015 | Kishioka et al. | |
| 2017/0101497 A1 | 4/2017 | Koguchi et al. | |

FOREIGN PATENT DOCUMENTS

| | | | |
|---|---|---|---|
| EP | 2878665 A1 | 6/2015 | |
| JP | H06-032800 A | 2/1994 | |
| JP | H07-113799 A | 5/1995 | |
| JP | H08-201384 A | 8/1996 | |
| JP | 2004-501110 A | 1/2004 | |
| JP | 2007-063459 A | 3/2007 | |
| JP | 2008-533489 A | 8/2008 | |
| JP | 2010-169604 A | 8/2010 | |
| JP | 2014-048278 A | 3/2014 | |
| JP | 2016-193976 A | 11/2016 | |
| WO | WO 2014/017513 A1 | 1/2014 | |
| WO | WO 2014/058061 A1 | 4/2014 | |
| WO | WO 2014/168230 A1 | 10/2014 | |
| WO | WO-2014168230 A1 * | 10/2014 | ........... C07K 14/705 |
| WO | WO 2016/002796 A1 | 1/2016 | |

OTHER PUBLICATIONS

Yoshida et al, WO 2014168230 Machine Translation, Oct. 16, 2014 (Year: 2014).*
Proks et al, 2012, Click and Seed Approach to the Biomimetic Modification of Material Surfaces, Macromol. Biosci, 12, 1232-1242 (Year: 2012).*
Nishida et al., "Optimization of the composition of zwitterionic copolymers for the easy-construction of bio-inactive surfaces," *J. Biomed. Mater. Res. A*, 104(8): 2029-2036 (2016).
Nishida et al., "Titanium allow modified with anti-biofouling zwitterionic polymer to facilitate formation of bio-mineral layer," *Colloids Surf. B: Biointerfaces*, 152: 302-310 (2017).

(Continued)

*Primary Examiner* — Jessica Whiteley
(74) *Attorney, Agent, or Firm* — Leydig, Voit & Mayer, Ltd.

(57) ABSTRACT

Provided are a ligand-bearing substrate which has a surface at least partially coated with a polymer (P3) containing structural units represented by the formulae (1a) and (1b) (in the formulae, $R^1$, $R^2$, X, Y, L, $Q^1$, $Q^2$, $Q^3$, m1, m2 and n are as described in the claims and description); a raw material for such a substrate; and a method for producing such substrates.

11 Claims, 5 Drawing Sheets
Specification includes a Sequence Listing.

(56) References Cited

OTHER PUBLICATIONS

Sobolčiak et al., "Photoimmobolization of zwitterionic polymers on surfaces to reduce cell adhesion," *J. Colloid Interface Sci.*, 500: 294-303 (2017).
European Patent Office, Supplementary European Search Report in European Patent Application No. 18831785.3 (dated May 4, 2020).
Lutz et al., "Efficient construction of therapeutics, bioconjugates, biomaterials and bioactive surfaces using azide-alkyne 'click' chemistry," *Advanced Drug Delivery Reviews*, 60(9): 958-970 (2008).
Lísalová, "Ultralow-Fouling Behavior of Biorecognition Coatings Based on Carboxy-Functional Brushes of Zwitterionic Homo- and Copolymers in Blood Plasma: Functionalization Matters," *Anal. Chemistry*, 89(6): 3524-3531 (2017).
Proks et al., "'Click & Seed' Approach to the Biomimetic Modification of Material Surfaces," *Macromol. Biosci.*, 12(9): 1232-1242 (2012).
Japanese Patent Office, International Search Report in International Patent Application No. PCT/JP2018/025820 (dated Oct. 9, 2018).

\* cited by examiner (A)　　　　(B)　　　　(C)　　　　(D)

(A)　　　　(B)　　　　(C)　　　　(D)

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Synthetic Sequence - Ligand

<400> SEQUENCE: 1

Gln Gln Gly Trp Phe Pro
1               5

<210> SEQ ID NO 2
<211> LENGTH: 20
<212> TYPE: PRT
<213> ORGANISM: Artificial Sequence
<220> FEATURE:
<223> OTHER INFORMATION: Synthetic Sequence - Ligand

<400> SEQUENCE: 2

Phe Asp Ala Ile Ala Glu Ile Gly Asn Gln Leu Tyr Leu Phe Lys Asp
1               5                   10                  15

Gly Lys Tyr Trp
            20

<210> SEQ ID NO 3
<211> LENGTH: 11
<212> TYPE: PRT
<213> ORGANISM: Artificial Sequence
<220> FEATURE:
<223> OTHER INFORMATION: Synthetic Sequence - Ligand
<220> FEATURE:
<221> NAME/KEY: BINDING
<222> LOCATION: (10)..(10)
<223> OTHER INFORMATION: Azidohomoalanine

<400> SEQUENCE: 3

Gln Gln Gly Trp Phe Pro Gly Gly Gly Xaa Gly
1               5                   10

<210> SEQ ID NO 4
<211> LENGTH: 22
<212> TYPE: PRT
<213> ORGANISM: Artificial Sequence
<220> FEATURE:
<223> OTHER INFORMATION: Synthetic Sequence - Ligand
<220> FEATURE:
<221> NAME/KEY: BINDING
<222> LOCATION: (21)..(21)
<223> OTHER INFORMATION: Azidohomoalanine
```

```
<400> SEQUENCE: 4

Gln Gln Gly Trp Phe Pro Gly Ala Gly Ala Gly Ala Gly Ala
1               5                   10                  15

Gly Ala Gly Ala Xaa Gly
                20

<210> SEQ ID NO 5
<211> LENGTH: 8
<212> TYPE: PRT
<213> ORGANISM: Artificial Sequence
<220> FEATURE:
<223> OTHER INFORMATION: Synthetic Sequence - Ligand
<220> FEATURE:
<221> NAME/KEY: BINDING
<222> LOCATION: (7)..(7)
<223> OTHER INFORMATION: Azidohomoalanine

<400> SEQUENCE: 5

Gln Gln Gly Trp Phe Pro Xaa Gly
1               5
```

SUBSTRATES COATED WITH SELECTIVE CELL SEPARATION OR CELL CULTURE POLYMERS

CROSS-REFERENCE TO RELATED APPLICATIONS

This patent application is the U.S. national phase of International Patent Application No. PCT/JP2018/025820, filed on Jul. 9, 2018, which claims the benefit of Japanese Patent Application No. 2017-135585, filed on Jul. 11, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,795 bytes ASCII (Text) file named "747180SequenceListing.txt," created Jan. 6, 2020.

TECHNICAL FIELD

The present invention relates to a substrate coated with a polymer containing non-cell adhesive structural units and cell adhesive structural units, to a raw material for such a substrate, and to a method for producing such substrates. In particular, the present invention relates to a substrate coated with a polymer for selective cell separation or cell culture of which cell adhesive structural units contains a peptide, an antibody, a protein or a low-molecular compound capable of acting as a ligand with respect to a specific cell, and also relates to a method for producing such substrates.

BACKGROUND ART

Molecules such as peptides, antibodies, proteins and low-molecular compounds can act as ligands with respect to specific cells. Cells are caused to be selectively adhered to these ligands and are thereby separated. Numerous cell separation methods and separation materials which utilize this cell selectivity have been reported. For example, lymphotoxin is immobilized onto a 96-well plate, plastic beads or the like to form a carrier, and cells having a lymphotoxin receptor are selectively adsorbed to the carrier (see, for example, Patent Literature 1).

Further, a cell separation method has been reported which comprises a step of covalently bonding a molecule such as a monoclonal or polyclonal antibody capable of binding to an antigen expressed on the surface of cells which are to be isolated, to a carboxyl compound having a molecular weight of not more than 10,000 to form a modified antibody, a step of reacting the modified antibody with a cell fluid such as a cell suspension containing the target cells and thereby causing the modified antibody to bind to the target cells, a step of treating the modified antibody-cell composite fluid with a water insoluble carrier having an amino group or an imino group on the surface so as to cause the target cells to bind to the carrier and also removing the undesired materials such as other cells, and a step of disassociating the target cells alone from the carrier using an appropriate technique (see, for example, Patent Literature 2). In this separation method, the water insoluble carrier having an amino group or an imino group on the surface which is used for the recovery of the modified antibody-cell composite may be specifically one prepared by impregnating a nonwoven fabric with polyethylene diacrylate and polyethylenimine and grafting the compounds by electron beam irradiation.

Further, a cell selective filter has been reported, characterized in that a specific peptide or protein is immobilized on a nonwoven fabric that is composed of fibers having at least an aromatic ring and/or a polyolefin chain, wherein the peptide or protein has an amino acid sequence capable of forming a complementarity determining region in an amino acid sequence constituting a cell-specific heavy chain or light chain variable region, wherein the fibers have an average fiber diameter of not less than 1 μm and not more than 100 μm, and wherein the aromatic ring and/or the polyolefin chain are substituted with at least two or more halogen atoms or halogen analogue substituents at an alpha carbon and/or beta carbon of carbonyl carbon (see, for example, Patent Literature 3).

CITATION LIST

Patent Literature

Patent Literature 1: Japanese Patent Application Kokai Publication No. H6-32800
Patent Literature 2: Japanese Patent Application Kokai Publication No. H7-113799
Patent Literature 3: Japanese Patent Application Kokai Publication No. H8-201384

SUMMARY OF INVENTION

Technical Problem

The conventional techniques described above, however, have drawbacks in that the immobilization of ligands to substrates (such as beads, plates and filters) is insufficient, and in that the cell selectivity of ligands is deteriorated due to the nonspecific adhesion of cells to ligand-carrying compounds (polymers) or bases themselves.

Solution to Problem

The present inventors have carried out extensive studies on coating materials which have high binding with respect to substrates and which have function of inhibiting adhesion of biological substances such as cells. Based on the knowledge obtained so far, the present inventors have found that a substrate which is coated with a polymer containing non-cell adhesive structural units and cell adhesive structural units maintains cell selectivity without suffering nonspecific binding of cells to the polymer or the base itself, and thereby exhibits outstanding selective cell culture performance and cell separation performance. The present invention has been completed based on the finding.

A summary of the present invention is as described below.

[1] A ligand-bearing substrate having a surface at least partially coated with a polymer (P3) containing structural units represented by the following formulae (1a) and (1b):

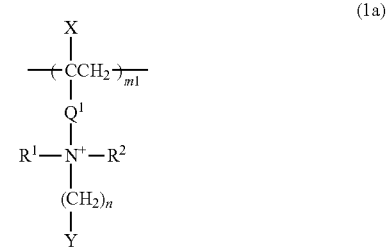

(1a)

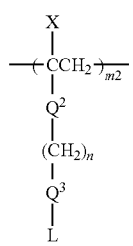

[wherein $R^1$ and $R^2$ each independently denote a C1-C5 linear alkyl group, X denotes a hydrogen atom or a C1-C5 linear alkyl group, Y denotes a carboanion (—COO$^-$ group) or a sulfoanion (—SO$_3^-$ group), L denotes a ligand, $Q^1$ and $Q^2$ each independently denote an ester bond, a phosphodiester bond, an amide bond, a C1-C10 linear or branched alkylene group or an optionally substituted phenylene group, or a divalent group composed of a combination of any of the above bonds and groups, $Q^3$ denotes a divalent organic group containing a 1,2,3-triazole ring skeleton, m1 and m2 each independently denote an integer of 1 to 200, and n independently at each occurrence denotes an integer of 1 to 10].

[2] A ligand-bearing substrate having a surface at least partially coated with a polymer (P2) containing a non-cell adhesive structural unit and a structural unit containing a ligand.

[3] The ligand-bearing substrate described in [1] or [2], wherein the ligand is selected from the group consisting of peptides, antibodies, proteins and low-molecular compounds.

[4] The ligand-bearing substrate described in [3], wherein the peptide contains Gln-Gln-Gly-Trp-Phe sequence.

[5] A substrate having a surface at least partially coated with a polymer (P1) containing a non-cell adhesive structural unit and a cell adhesive structural unit.

[6] The substrate described in any of [1] to [5], which is a cell separation substrate.

[7] The substrate described in any of [1] to [5], which is a cell culture substrate.

[8] A substrate having a surface at least partially coated with a polymer (P4) containing a non-cell adhesive structural unit and a structural unit containing a carbon-carbon triple bond or an azide group.

[9] A substrate having a surface at least partially coated with a polymer (P5) containing structural units represented by the following formulae (1a) and (1c):

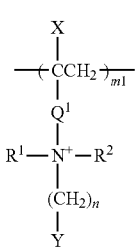

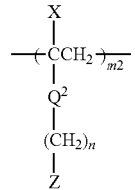

(wherein $R^1$, $R^2$, X, Y, $Q^1$, $Q^2$, m1, m2 and n are the same as described in [1], and Z denotes a group containing a carbon-carbon triple bond or containing azide).

[10] The substrate described in any of [1] to [9], wherein the substrate is a dish, a plate, a porous film, a particle or a filter.

[11] A composition containing a polymer (P5) containing structural units represented by the following formulae (1a) and (1c), and a solvent:

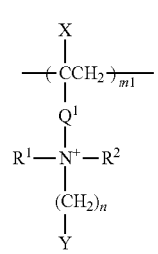

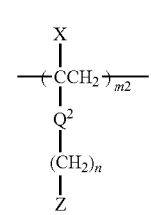

(wherein $R^1$, $R^2$, X, Y, Z, $Q^1$, $Q^2$, m1, m2 and n are the same as described in [9]).

[12] A method for producing a ligand-bearing substrate, comprising a step of bringing a ligand containing a carbon-carbon triple bond or an azide group into contact with the substrate described in [8] or [9].

[13] A method for producing a ligand-bearing substrate, comprising a step of applying the composition described in [11] to a substrate to form a polymer (P5)-coated substrate, and a step of bringing a ligand containing a carbon-carbon triple bond or an azide group into contact with the coated substrate.

[14] A method for imparting cell adhesion properties to a substrate, comprising providing a substrate having a surface at least partially coated with a polymer (P4) containing a non-cell adhesive structural unit and a structural unit containing a carbon-carbon triple bond or an azide group, and bringing a ligand containing an azide group or a carbon-carbon triple bond into contact with the substrate.

[15] The substrate described in [6], which is capable of allowing at least one type of cells to be selectively separated from a cell mixture fluid containing at least two or more types of cells.

[16] A cell separation method using the substrate described in any of [1] to [5].

[17] The substrate described in [7], which is capable of allowing at least one type of cells to be selectively cultured from a cell mixture fluid containing at least two or more types of cells.

[18] A cell culture method using the substrate described in any of [1] to [5].

[19] The ligand-bearing substrate described in [1], wherein the polymer (P3) further contains a structural unit represented by the following formula (1d):

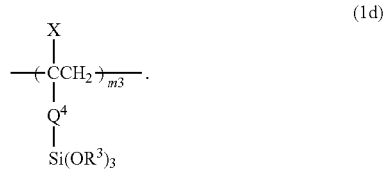

(wherein $R^3$ independently at each occurrence denotes a C1-C5 linear alkyl group, X denotes a hydrogen atom or a C1-C5 linear alkyl group, $Q^4$ denotes an ester bond, a phosphodiester bond, an amide bond, a C1-C10 linear or branched alkylene group or an optionally substituted phenylene group, or a divalent group composed of a combination of any of the above bonds and groups, and m3 denotes an integer of 1 to 200).

[20] The substrate described in [9], wherein the polymer (P5) further contains a structural unit represented by the following formula (1d):

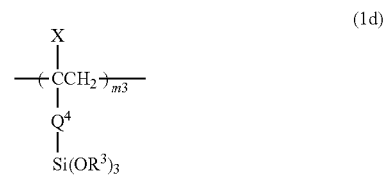

(wherein $R^3$ independently at each occurrence denotes a C1-C5 linear alkyl group, X denotes a hydrogen atom or a C1-C5 linear alkyl group, $Q^4$ denotes an ester bond, a phosphodiester bond, an amide bond, a C1-C10 linear or branched alkylene group or an optionally substituted phenylene group, or a divalent group composed of a combination of any of the above bonds and groups, and m3 denotes an integer of 1 to 200).

[21] The composition described in [11], wherein the polymer (P5) further contains a structural unit represented by the following formula (1d):

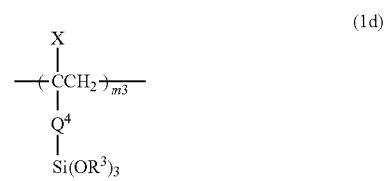

(wherein $R^3$ independently at each occurrence denotes a C1-C5 saturated linear alkyl group, X denotes a hydrogen atom or a C1-C5 linear alkyl group, $Q^4$ denotes an ester bond, a phosphodiester bond, an amide bond, a C1-C10 linear or branched alkylene group or an optionally substituted phenylene group, or a divalent group composed of a combination of any of the above bonds and groups, and m3 denotes an integer of 1 to 200).

Advantageous Effects of Invention

The substrates of the present invention which are coated with a polymer containing non-cell adhesive structural units and cell adhesive structural units maintain cell selectivity without suffering nonspecific adhesion of cells to the polymer or the substrate itself, and thereby exhibit outstanding selective cell culture performance and cell separation performance. When, in particular, the cell adhesive structural units contain a peptide, an antibody, a protein or a low-molecular compound capable of acting as a ligand with respect to a specific cell, the polymer-coated substrate has an excellent binding of the polymer to the substrate by virtue of its having the non-cell adhesive structural units. In addition to this, it also maintains ligand's cell selectivity because the polymer and the substrate themselves except the ligand moieties are non-adhesive to cells, thus attaining excellent selective cell culture performance and cell separation performance.

BRIEF DESCRIPTION OF DRAWINGS

capture rate evaluation in Example 5. FIG. 6(A) shows the counts of cells adhered to the surface of the peptide-carrying-polymer-coated glass plate (Example 2), and FIG. 6(B) shows the results of the flow cytometry of the glass plate.

FIG. 7(A) shows the counts of cells adhered to the surface of the peptide-carrying-polymer-coated glass plate (Example 2), and FIG. 7(B) shows the results of the flow cytometry of the glass plate.

DESCRIPTION OF EMBODIMENTS ((Description of Terms))

Figure 1:
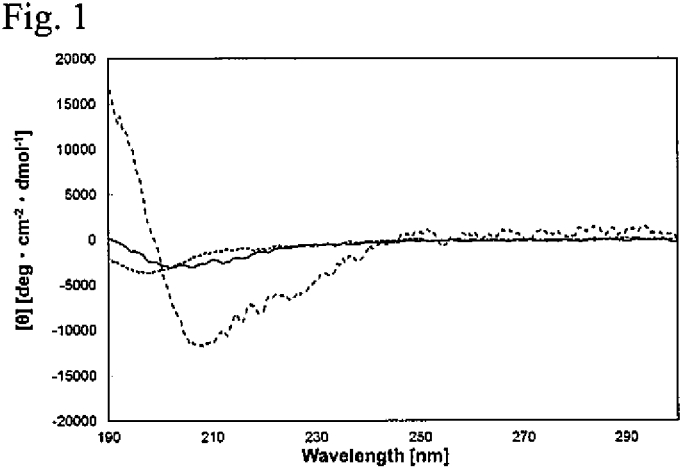
FIG. 1 shows CD spectra obtained by circular dichroism (CD) spectroscopy of peptides 1 to 3 prepared in Synthetic Example 1. The solid line is the spectrum of peptide 1, the dotted line the spectrum of peptide 2, and the long broken line the spectrum of peptide 3.

The terms used in the present invention have the definitions described below unless otherwise mentioned.

In the present invention, "halogen atom" means a fluorine atom, a chlorine atom, a bromine atom or an iodine atom.

In the present invention, "alkyl group" means an acyclic or cyclic, saturated aliphatic monovalent hydrocarbon group. Examples of the "C1-C5 linear or branched alkyl groups" include methyl group, ethyl group, n-propyl group, isopropyl group, n-butyl group, isobutyl group, s-butyl group, t-butyl group, n-pentyl group, 1-methylbutyl group, 2-methylbutyl group, 3-methylbutyl group, 1,1-dimethylpropyl group, 1,2-dimethylpropyl group, 2,2-dimethylpropyl group and 1-ethylpropyl group. In particular, the "C1-C5 linear alkyl group" may be a methyl group, an ethyl group, an n-propyl group, an n-butyl group or an n-pentyl group.

In the present invention, "alkynyl group" means a linear or branched, unsaturated aliphatic monovalent hydrocarbon group containing at least one carbon-carbon triple bond. Examples of the "C2-C5 alkynyl groups" include ethynyl group, propargyl group, 3-butynyl group and 4-pentynyl group.

In the present invention, "ester bond" means —C(=O)—O— or —O—C(=O)—, "phosphodiester bond" means —O—P(=O)(—O⁻)—O—, "amide bond" means —NHC(=O)— or —C(=OL)NH—, "ether bond" means —O—, "amino bond" means —NH—, "carbonyl bond" means —C(=O)—, and "thioether bond" means —S—.

In the present invention, "optionally substituted phenylene group" means "phenylene group" or "substituted phenylene group". Examples of the "phenylene groups" include 1,4-phenylene group, 1,3-phenylene group and 1,2-phenylene group, with 1,4-phenylene group being preferable. Examples of the "substituted phenylene groups" include 1,4-phenylene group, 1,3-phenylene group and 1,2-phenylene group each substituted with at least one substituent selected from, for example, halogen atoms and C1-C5 linear or branched alkyl groups.

In the present invention, "alkylene group" means a linear or branched, saturated aliphatic divalent hydrocarbon group. Examples of the "C1-C10 linear or branched alkylene groups" include methylene group, ethylene group, propylene group, trimethylene group, tetramethylene group, 1-methylpropylene group, 2-methylpropylene group, dimethylethylene group, ethylethylene group, pentamethylene group, 1-methyl-tetramethylene group, 2-methyl-tetramethylene group, 1,1-dimethyl-trimethylene group, 1,2-dimethyl-trimethylene group, 2,2-dimethyl-trimethylene group, 1-ethyl-trimethylene group, hexamethylene group, octamethylene group and decamethylene group, with ethylene group, propylene group, octamethylene group and decamethylene group being preferable. For example, C1-C5 linear or branched alkylene groups such as ethylene group, propylene group, trimethylene group and tetramethylene group are more preferable, and ethylene group and propylene group are particularly preferable.

In the present invention, (meth)acrylate compounds are a collective term for acrylate compounds and methacrylate compounds. For example, (meth)acrylic acid means acrylic acid and methacrylic acid.

Examples of the cells in the present invention include fibroblasts, bone marrow cells, B lymphocytes, T lymphocytes, neutrophils, red blood cells, platelets, macrophages, monocytes, bone cells, bone marrow cells, pericytes, dendritic cells, keratinocytes, fat cells, mesenchymal cells, epithelial cells, epidermal cells, endothelial cells, vascular endothelial cells, hepatic parenchymal cells, cartilage cells, cumulus cells, neural cells, glial cells, neurons, oligodendrocyte, microglia, astroglial cells, heart cells, esophagus cells, muscle cells (for example, smooth muscle cells and skeletal muscle cells), pancreatic beta cells, melanocytes, hematopoietic precursor cells, mononuclear cells, embryonic stem cells (ES cells), embryonic tumor cells, embryonic germline stem cells, induced pluripotent stem cells (iPS cells), neural stem cells, hematopoietic stem cells, mesenchymal stem cells, liver stem cells, pancreatic stem cells, muscle stem cells, germline stem cells, intestinal stem cells, cancer stem cells, hair follicle stem cells, megakaryocytes, CD34 positive spinal cord-derived megakaryocytes, and various cell lines (for example, HCT116, Huh7, HEK293 (human embryonic kidney cells), HeLa (human cervical cancer cell lines), HepG2 (human liver cancer cell lines), UT7/TPO (human leukemia cell lines), CHO (Chinese hamster ovary cell lines), MDCK, MDBK, BHK, C-33A, HT-29, AE-1, 3D9, Ns0/1, Jurkat, NIH3T3, PC12, 52, Sf9, Sf21, High Five, Vero). Of these, mesenchymal stem cells are preferable.

In general, cell adhesive is a term indicating a process in which a cell adhesion-promoting protein (such as, for example, fibronectin or vitronectin, or laminin) adsorbs to a substrate and interacts with an integrin receptor on a cell membrane to bind the cell thereto, or a process in which cells are attached to one another by the interaction of cadherins which are receptors present on the cell membranes. The meaning of cell adhesive in the present invention slightly differs from the general meaning of cell adhesive in that a ligand capable of interacting with a receptor specifically expressed on a cell membrane is immobilized beforehand to a substrate and is allowed to interact with a receptor present on the membranes of specific cells to capture the cells.

On the other hand, non-cell adhesive is a term meaning that cells do not respond to or interact with a substrate, and this meaning also applies in the present invention. Usually, proteins too often cannot adsorb to the surface of such a substrate because cell-substrate adhesion in most cases is an integrin-dependent adhesion mediated by a protein adsorbed on the substrate. It can be therefore said that a function irresponsive to biological substances needs to be added to the surface to construct a non-cell adhesive substrate.

((Description of Invention))

The present invention pertains to a substrate having a surface at least partially coated with a polymer (P1) containing a non-cell adhesive structural unit and a cell adhesive structural unit. The substrate is not particularly limited as long as at least part of the surface has at least a coating film with a film thickness of not more than 1500 nm, preferably 10 to 1300 nm, more preferably 10 to 1100 nm, still more preferably 10 to 1000 nm, and particularly preferably 10 to 500 nm. The surface coverage ratio is preferably not less than 10%, more preferably not less than 20%, still more preferably not less than 30%, particularly preferably not less than 40%, and most preferably not less than 50% of the total surface area of the substrate. When, for example, the substrate is a flat plate, it is preferable that the coating film covers not less than 10%, more preferably not less than 30%, still more preferably not less than 50%, and most preferably not less than 80% of the total surface area of one side.

In an embodiment of the present invention, the non-cell adhesive structural units in the polymer may be derived from an ethylenically unsaturated monomer. For example, the ethylenically unsaturated monomer may be one, or two or more kinds of ethylenically unsaturated monomers selected from the group consisting of (meth)acrylic acid and esters thereof; vinyl acetate; vinylpyrrolidone; ethylene; vinyl alcohols; and hydrophilic functional derivatives of these monomers.

Examples of the hydrophilic functional groups in the hydrophilic functional derivatives include phosphoric acid, phosphonic acid and ester structures thereof; betaine structures; amide structures; alkylene glycol residues; amino groups; and sulfinyl groups.

Here, the phosphoric acid and the ester structures thereof are groups represented by the following formula:

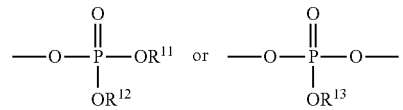

[wherein $R^{11}$, $R^{12}$ and $R^{13}$ are each independently a hydrogen atom or an organic group (such as, for example, a C1-C5 linear or branched alkyl group)]. The phosphonic acid and the ester structures thereof are groups represented by the following formula:

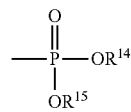

[wherein $R^{14}$ and $R^{15}$ are each independently a hydrogen atom or an organic group (such as, for example, a C1-C5 linear or branched alkyl group)]. Examples of the ethylenically unsaturated monomers having such a structure include acid phosphoxyethyl (meth)acrylate and vinylphosphonic acid.

The betaine structures are monovalent or divalent groups derived from compounds having an amphoteric center between a quaternary ammonium cation structure and an acidic anion structure. Examples thereof include phosphorylcholine group:

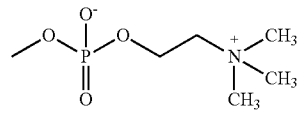

Examples of the ethylenically unsaturated monomers having such a structure include 2-methacryloyloxyethyl phosphorylcholine (MPC).

The amide structures are groups represented by the following formula:

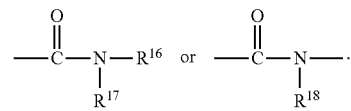

[wherein $R^{16}$, $R^{17}$ and $R^{18}$ are each independently a hydrogen atom or an organic group (such as, for example, a methyl group, a hydroxymethyl group or a hydroxyethyl group)]. Examples of the ethylenically unsaturated monomers having such a structure include (meth)acrylamide and N-(hydroxymethyl) (meth)acrylamide. Other monomers having such a structure are disclosed in literature such as, for example, Japanese Patent Application Kokai Publication No. 2010-169604.

The alkylene glycol residues are alkyleneoxy groups (-Alk-O—) which remain after alkylene glycols (HO-Alk-OH; wherein Alk is a C1-C10 linear or branched alkylene group) undergo condensation reaction via one or both of the terminal hydroxyl groups thereof with other compounds. The residues also include poly(alkyleneoxy) groups composed of alkyleneoxy repeating units. Examples of the ethylenically unsaturated monomers having such a structure include 2-hydroxyethyl (meth)acrylate and methoxypolyethylene glycol (meth)acrylate. Other monomers having such a structure are disclosed in literature such as, for example, Japanese Patent Application Kokai Publication No. 2008-533489.

The amino groups are groups represented by the formula: —$NH_2$, —$NHR^{19}$ or —$NR^{20}R^{21}$ [wherein $R^{19}$, $R^{20}$ and $R^{21}$ are each independently an organic group (such as, for example, a C1-C5 linear or branched alkyl group)]. The amino groups in the present specification include quaternized or chlorinated amino groups. Examples of the ethylenically unsaturated monomers having such a structure include dimethylaminoethyl (meth)acrylate, 2-(t-butylamino)ethyl (meth)acrylate and methacryloylcholine chloride.

The sulfinyl groups are groups represented by the following formula:

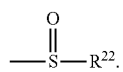

[wherein $R^{22}$ is an organic group (such as, for example, a C1-C10 organic group, preferably a C1-C10 alkyl group having one or more hydroxyl groups)]. Examples of the polymers having such a structure include copolymers disclosed in literature such as Japanese Patent Application Kokai Publication No. 2014-48278.

In an embodiment of the present invention, the non-cell adhesive structural units are preferably structural units represented by the following formula (1a).

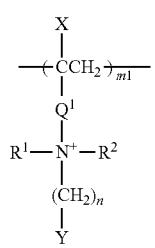

(1a)

In the above formula, $R^1$ and $R^2$ each independently denote a C1-C5 linear alkyl group, X denotes a hydrogen atom or a C1-C5 linear alkyl group, Y denotes a carboanion (—$COO^-$ group) or a sulfoanion (—$SO_3^-$ group), $Q^1$ denotes an ester bond, a phosphodiester bond, an amide bond, a C1-C10 linear or branched alkylene group or an optionally substituted phenylene group, or a divalent group composed of a combination of any of the above bonds and groups, m1 denotes an integer of 1 to 200, and n denotes an integer of 1 to 10.

It is preferable that the structural units be represented by the formula (1a) in which $R^1$ and $R^2$ each independently denote a methyl group or an ethyl group, X denotes a hydrogen atom or a methyl group, Y denotes a carboanion (—$COO^-$ group) or a sulfoanion (—$SO_3^-$ group), $Q^1$ denotes an ester bond, an amide bond, a C1-C10 linear or branched alkylene group, or a divalent group composed of a combination of any of the above bonds and groups, m1 denotes an integer of 1 to 200, and n denotes an integer of 1 to 10. It is more preferable that the structural units be represented by the formula (1a) in which $R^1$ and $R^2$ denote methyl groups, X denotes a hydrogen atom or a methyl group, Y denotes a carboanion (—$COO^-$ group), $Q^1$ denotes —C(=O)—O—, -$Alk^1$— or —C(=O)—O-$Alk^{1-}$, m1 denotes an integer of 1 to 200, and n denotes an integer of 1 to 10. Incidentally, $Alk^1$ is a C1-C10 linear or branched alkylene group, preferably a C1-C5 linear or branched alkylene group, and more preferably a methylene group, an ethylene group or a propylene group.

Examples of the monomers capable of giving structural units of the formula (1a) include N-methacryloyloxyethyl-N,N-dimethylammonium-a and N-methylcarboxybetaine.

In an embodiment of the present invention, the cell adhesive structural units in the polymer preferably contain a ligand. That is, the polymer which covers at least a portion of the surface of the substrate is preferably a polymer (P2) containing non-cell adhesive structural units and structural units containing a ligand.

In an embodiment of the present invention, the cell adhesive structural units are more preferably structural units represented by the following formula (1b). That is, the polymer which covers at least a portion of the surface of the substrate is preferably a polymer (P3) containing structural units of the formula (1a) described hereinabove and structural units represented by the following formula (1b).

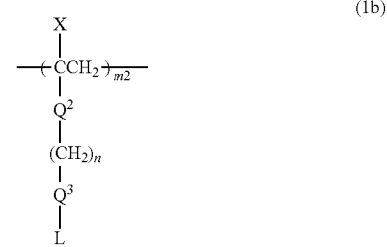

In the above formula, X denotes a hydrogen atom or a C1-C5 linear alkyl group, L denotes a ligand, $Q^2$ denotes an ester bond, a phosphodiester bond, an amide bond, a C1-C10 linear or branched alkylene group or an optionally substituted phenylene group, or a divalent group composed of a combination of any of the above bonds and groups, $Q^3$ denotes a divalent organic group containing a 1,2,3-triazole ring skeleton, m2 denotes an integer of 1 to 200, and n denotes an integer of 1 to 10.

It is preferable that the structural units be represented by the formula (1b) in which X denotes a hydrogen atom or a methyl group, L denotes a ligand, $Q^2$ denotes an ester bond or an amide bond, $Q^3$ denotes a divalent group containing a structure represented by the following formula (2a) or (2b):

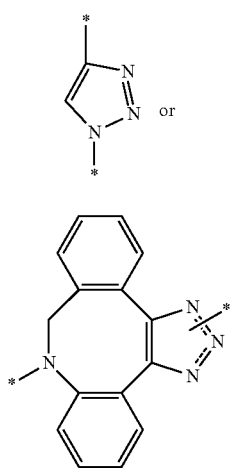

m2 denotes an integer of 1 to 200, and n denotes an integer of 1 to 10. It is more preferable that the structural units be represented by the formula (1b) in which X denotes a hydrogen atom or a methyl group, L denotes a ligand, $Q^2$ denotes an ester bond or an amide bond, and $Q^3$ is represented by the following formula (2a-1), (2a-2), (2b-1) or (2b-2):

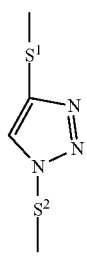

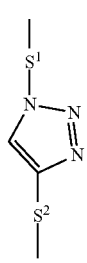

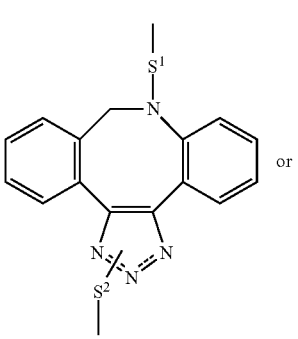

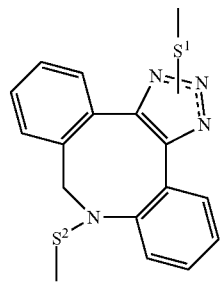

(wherein $S^1$ and $S^2$ denote divalent groups resulting from azide-alkyne cycloaddition reaction).

In an embodiment of the present invention, the structural units of the formula (1b) are more preferably structural units represented by any of the following formulae (1b-1) to (1b-4):

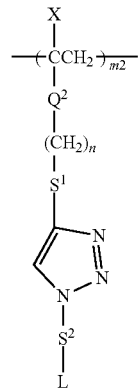

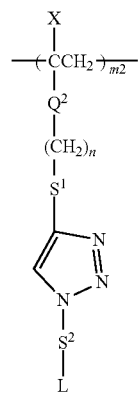

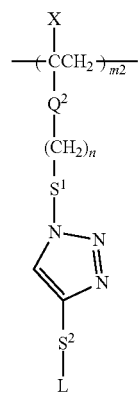

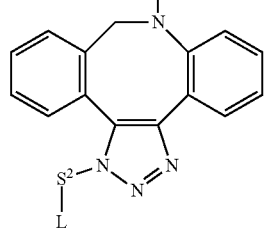

(1b-4)

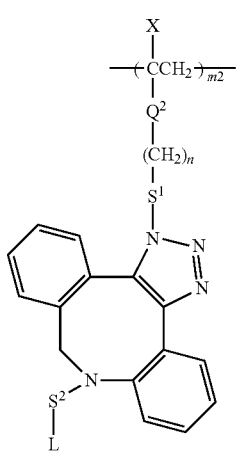

In the above formulae, X denotes a hydrogen atom or a C1-C5 linear alkyl group, L denotes a ligand, $Q^2$ denotes an ester bond, a phosphodiester bond, an amide bond, a C1-C10 linear or branched alkylene group or an optionally substituted phenyl=group, or a divalent group composed of a combination of any of the above bonds and groups, $S^1$ and $S^2$ each independently denote a single bond, an ester bond, an amide bond, an ether bond, an amino bond, a carbonyl bond, a thioether bond, a C1-C5 linear or branched alkylene group, or a divalent group composed of a combination of any of the above bonds and groups, m2 denotes an integer of 1 to 200, and n denotes an integer of 1 to 10.

It is more preferable that the structural units be represented by any of the formulae (1b-1) to (1b-4) in which X denotes a hydrogen atom or a methyl group, L denotes a ligand, $Q^2$ denotes an ester bond or an amide bond, $S^1$ and $S^2$ each independently denote a single bond, an ester bond or a C1-C5 linear or branched alkylene group, m2 denotes an integer of 1 to 200, and n denotes an integer of 1 to 10. The structural units are still more preferably represented by the formula (1b-1) or (1b-2), and particularly preferably represented by the formula (1b-1).

In an embodiment of the present invention, the ligand is selected from the group consisting of peptides, antibodies, proteins and low-molecular compounds. Examples include such peptides as peptide hormones (e.g., insulin) and neuropeptides; such antibodies as IgG, IgA and IgM; such proteins as fibrinogens, bovine serum albumins (BSA), ovalbumins, human albumins, various globulins, serum γ-globulins, β-lipoproteins, lysozymes, fibronectins, pepsins, histones, collagens and various lectins; and such low-molecular compounds as sugars (e.g., glucose, galactose, mannose, fructose), nucleosides and nucleotides.

In an embodiment of the present invention, the ligand is preferably a peptide, and is more preferably a peptide containing Gln-Gln-Gly-Trp-Phe-Pro sequence (SEQ ID NO: 1) or Phe-Asp-Ala-Ile-Ala-Glu-Ile-Gly-Asn-Gln-Leu-Tyr-Leu-Phe-Lys-Asp-Gly-Lys-Tyr-Tr p sequence (SEQ ID NO: 2).

From the foregoing, the polymer (P3) which covers at least a portion of the surface of the substrate in an embodiment of the present invention is a polymer which contains structural units represented by the following formulae (1a) and (1b):

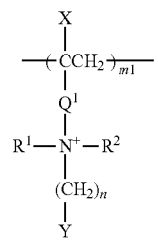
(1a)

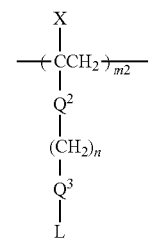
(1b)

(wherein $R^1$, $R^2$, X, Y, L, $Q^1$, $Q^2$, $Q^3$, m1, m2 and n are the same as described hereinabove), and is particularly preferably a polymer which contains structural units represented by the following formulae (1a) and (1b-1):

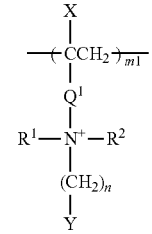
(1a)

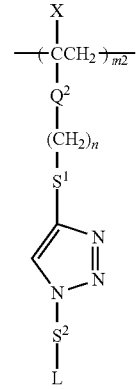
(1b-1)

(wherein $R^1$, $R^2$, X, Y, L, $Q^1$, $Q^2$, $S^1$, $S^2$, m1, m2 and n are the same as described hereinabove).

The polymer (P3) of the present application may further contain structural units represented by the following formula (1d). It is expected that the polymer containing such structural units will attain adhesion with respect to a substrate, in particular, to a substrate having a hydroxyl group on the surface (for example, a glass plate).

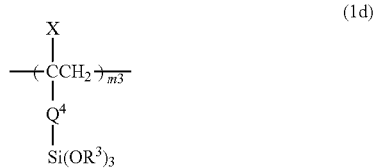

(1d)

In the above formula, $R^3$ independently at each occurrence denotes a C1-C5 linear alkyl group, X denotes a hydrogen atom or a C1-C5 linear alkyl group, $Q^4$ denotes an ester bond, a phosphodiester bond, an amide bond, a C1-C10 linear or branched alkylene group or an optionally substituted phenylene group, or a divalent group composed of a combination of any of the above bonds and groups, and m3 denotes an integer of 1 to 200.

In an embodiment of the present invention, the structural units of the formula (1d) are preferably structural units represented by the following formula (1d-1).

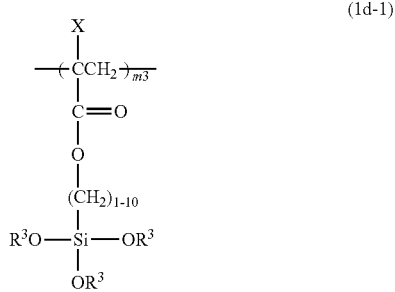

(1d-1)

In the above formula, $R^3$, X and m3 are the same as defined in the formula (1d).

Examples of the monomers capable of giving structural units of the formula (1d) include monomers containing a phenylene group such as p-styryltrimethoxysilane, and monomers containing an ester bond and a divalent group composed of a C1-C10 linear or branched alkylene group, such as 3-(meth)acryloyloxypropyltrimethoxysilane, 4-(meth)acryloyloxypropyltriethoxysilane and 3-(meth)acryloyloxypropyltriisopropoxysilane.

In an embodiment of the present invention, the polymers (P1) to (P3) may contain additional structural units such as, for example, those represented by the formula (1d) described above, in addition to the non-cell adhesive structural units (for example, structural units represented by the formula (1a) described hereinabove) and the cell adhesive structural units (for example, structural units represented by the formula (1b) described hereinabove) while still achieving the objects of the present invention. The molecular weight of the polymers (P1) to (P3) may be about several thousands to several millions, and is preferably 5,000 to 5,000,000, more preferably 5,000 to 2,000,000, and still more preferably 5,000 to 1,000,000. The structural units in the polymers (P1) to (P3) may be arranged in any manner without limitation, and the polymers (P1) to (P3) may be random, block, alternate and/or graft copolymers. The proportion of the non-cell adhesive structural units in the polymers (P1) to (P3), in particular, the proportion of the structural units of the formula (1a) in the polymer (P3) is 3 mol % to 80 mol % relative to all the structural units. The polymer (P3) may contain two or more kinds of structural units represented by the formula (1a). The proportion of the cell adhesive structural units in the polymers (P1) to (P3), in particular, the proportion of the structural units of the formula (1b) in the polymer (P3) is 3 mol % to 80 mol % relative to all the structural units. The polymer (P3) may contain two or more kinds of structural units represented by the formula (1b).

The polymers (P1) to (P3) may contain structural units other than the structural units represented by the formula (1d). Examples of the monomers capable of giving such additional structural units include (meth)acrylic acid, (meth) acrylate ester compounds, (meth)acrylamide compounds, vinyl compounds, styrene compounds, maleimide compounds, maleic anhydride and (meth)acrylonitrile. Specific examples include acrylate ester compounds such as methyl acrylate, ethyl acrylate, isopropyl acrylate, tert-butyl acrylate, isobutyl acrylate, n-hexyl acrylate, cyclohexyl acrylate, benzyl acrylate, phenyl acrylate and allyl acrylate, methacrylate ester compounds such as methyl methacrylate, ethyl methacrylate, isopropyl methacrylate, tert-butyl methacrylate, isobutyl acrylate, n-hexyl methacrylate, cyclohexyl methacrylate, benzyl methacrylate, phenyl methacrylate and allyl acrylate, acrylamide compounds such as N-methylacrylamide, N-ethylacrylamide, N-benzylacrylamide and N-phenylacrylamide, methacrylamide compounds such as methacrylamide, N-methylmethacrylamide, N-ethylmethacrylamide, N-benzylmethacrylamide and N-phenylmethacrylamide, vinyl compounds such as ethyl vinyl ether, benzyl vinyl ether and vinyl acetate, styrene compounds such as styrene and methoxystyrene, and maleimide compounds such as maleimide, N-methylmaleimide, N-phenylmaleimide and N-cyclohexylmaleimide.

In an embodiment of the present invention, the substrate having a surface at least partially coated with any of the polymers (P1) to (P3) may be used to separate or culture cells.

The substrate of the present invention may be used as a substrate capable of allowing at least one type of cells to be selectively separated from a cell mixture fluid containing at least two or more types of cells.

The cell mixture fluid is not particularly limited as long as the fluid contains at least two or more types of cells. Examples thereof include bloods, cell populations after differentiation induction, cell mixture fluids containing undifferentiated cultured stem cells and disorderly differentiated cells, and hMSC-HEK293 cell mixture fluids.

Preferably, the substrate is capable of allowing one or two types of cells to be selectively separated from three different types of cells. More preferably, the substrate is capable of allowing one type of cells to be selectively separated from two different types of cells.

For example, the substrate can separate the target cells from a mixture fluid in a ratio of, in order of preference, not less than 90 mass %, not less than 70 mass %, not less than 50 mass %, not less than 30 mass %, or not less than 10 mass % of the seeding amount.

In an embodiment of the present invention, the substrate having a surface at least partially coated with any of the polymers (P1) to (P3) may be prepared by applying any of the polymers (P1) to (P3) to a substrate. The polymers (P1) to (P3) may be applied to substrates by any technique without limitation, and known techniques may be used appropriately. The term "apply" comprehends various actions such as to soak the substrate into the polymer or a polymer solution, and to cast the polymer or a polymer solution over the substrate and allow the substrate to stand for a predetermined time. The substrate may be soaked or allowed to stand for an appropriate amount of time at an appropriate temperature which are selected in accordance with the material of the substrate and the kind of the polymer. For example, these treatments may be performed at 10 to 35° C., preferably ambient temperatures (for example, 25° C.), for 30 seconds to 24 hours, preferably 1 minute to 3 hours. In the manner described above, the surface of the substrate is coated at least partially, preferably over the entirety thereof, with any of the polymers (P1) to (P3).

In another embodiment of the present invention, the ligand-containing structural units in the polymers (P2) and (P3) may be usually introduced into the polymer by providing a polymer which contains structural units containing a specific reactive group, and reacting the specific reactive group in the polymer with a ligand containing a group capable of reacting with the reactive group. Such a reaction is known to those skilled in the art and is not particularly limited. A typical reaction is a click reaction. In particular, a click reaction based on azide-alkyne cycloaddition reaction is preferable. The reaction may be performed on the polymer applied to a substrate.

In another embodiment of the present invention, the ligand-containing structural units may be introduced into the polymer by a click reaction based on azide-alkyne cycloaddition reaction in which (i) structural units containing a carbon-carbon triple bond are brought into contact with a ligand containing an azide group, or (ii) structural units containing an azide group are brought into contact with a ligand containing a carbon-carbon triple bond.

That is, the present invention also pertains to a substrate having a surface at least partially coated with a polymer (P4) containing non-cell adhesive structural units and structural units containing a carbon-carbon triple bond or an azide group.

In an embodiment of the present invention, the structural units containing a carbon-carbon triple bond or an azide group are preferably structural units represented by the following formula (1c). Thus, the polymer which covers at least a portion of the surface of the substrate may be a polymer (P5) containing structural units of the formula (1a) described hereinabove and structural units represented by the following formula (1c).

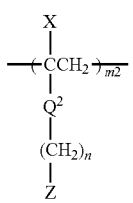

(1c)

In the above formula, X denotes a hydrogen atom or a C1-C5 linear alkyl group, Z denotes a group containing a carbon-carbon triple bond or containing an azide group, $Q^2$ denotes an ester bond, a phosphodiester bond, an amide bond, a C1-C10 linear or branched alkylene group or an optionally substituted phenylene group, or a divalent group composed of a combination of any of the above bonds and groups, m2 denotes an integer of 1 to 200, and n denotes an integer of 1 to 10.

The "group containing a carbon-carbon triple bond" denoted by Z is a group containing a carbon-carbon triple bond skeleton such as, for example, acetylene or dibenzylcyclooctyne represented by the following formula:

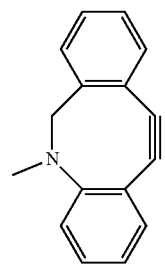 [SMILES: CN1Cc2ccccc2C#Cc2ccccc21]

Examples of such groups include those groups of the formula: —$S^{a1}$—$R^{a1}$ (wherein $S^{a1}$ is a single bond, an ester bond, an amide bond, an ether bond, an amino bond, a carbonyl bond, a thioether bond, a C1-C5 linear or branched alkylene group, or a divalent group composed of a combination of any of the above bonds and groups, and $R^{a1}$ is a C2-C5 alkynyl group or dibenzylcyclooctyne).

The "group containing azide" denoted by Z is a group which contains azide (—$N_3$). Examples of such groups include those groups of the formula: —$S^{a2}$-$N_3$ (wherein $S^{a2}$ is a single bond, an ester bond, an amide bond, an ether bond, an amino bond, a carbonyl bond, a thioether bond, a C1-C5 linear or branched alkylene group, or a divalent group composed of a combination of any of the above bonds and groups).

In particular, the structural units are preferably represented by the formula (1c) in which X denotes a hydrogen atom or a methyl group, Z denotes a group of the formula: —$S^{a2}$—$N_3$ (wherein $S^{a2}$ is a C1-C5 linear or branched alkylene group), $Q^2$ denotes an ester bond or an amide bond, m2 denotes an integer of 1 to 200, and n denotes an integer of 1 to 10. Examples of the monomers capable of giving such structural units of the formula (1c) include 3-azidopropyl methacrylate.

Also preferably, the structural units are represented by the formula (1c) in which X denotes a hydrogen atom or a methyl group, Z denotes a group of the formula: —$S^{a1}$ (wherein $S^{a1}$ is a C1-C5 linear or branched alkylene group, and $R^{a1}$ is a C2-C5 alkynyl group), $Q^2$ denotes an ester bond or an amide bond, m2 denotes an integer of 1 to 200, and n denotes an integer of 1 to 10. Examples of the monomers capable of giving such structural units of the formula (1c) include propargyl methacrylate.

Similarly to the polymer (P3) of the present application, the polymer (P5) of the present application may further contain structural units represented by the following formula (1d).

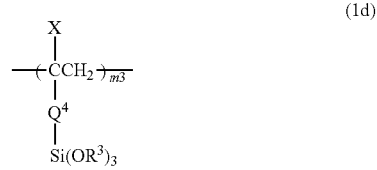

(1d)

In the above formula, $R^3$, X, $Q^4$ and m3 are the same as defined hereinabove. Preferred embodiments of the structural units of the formula (1d), and examples of the monomers capable of giving structural units of the formula (1d) are also the same as in the case of the polymer (P3).

In an embodiment of the present invention, for example, the polymer (P5) is not particularly limited as long as the polymer contains structural units of the formula (1a), structural units of the formula (1c) and optionally additional structural units (for example, structural units of the formula (1d)). Examples of the monomers capable of giving such additional structural units other than those of the formula (1d) in the polymer (P5) are the same as those in the polymer (P3). The polymer (P5) is desirably one obtained by radical polymerization of a monomer capable of giving structural units of the formula (1a), a monomer capable of giving structural units of the formula (1c) and optionally an additional monomer.

In the polymer (P5), the proportion of the structural units of the formula (1a) is 3 mol % to 80 mol % relative to all the structural units. The polymer (P5) may contain two or more kinds of structural units represented by the formula (1a).

In the polymer (P5), the proportion of the structural units of the formula (1c) is 3 mol % to 80 mol %. The polymer (P5) may contain two or more kinds of structural units represented by the formula (1c).

The solvent in the polymerization reaction may be water, an organic solvent, or a mixture of such solvents. The solvent may be selected appropriately in accordance with the kinds and properties of the monomers to be polymerized, a polymerization initiator and the target polymer. Examples include water; ketones such as acetone, methyl ethyl ketone, methyl isobutyl ketone, methyl isoamyl ketone, methyl amyl ketone and cyclohexanone; alcohols such as methanol, ethanol, isopropanol, ethylene glycol monomethyl ether, ethylene glycol monoethyl ether, propylene glycol monomethyl ether and propylene glycol monoethyl ether; esters such as methyl acetate, ethyl acetate, propyl acetate, isopropyl acetate, butyl acetate, methyl propionate, methyl lactate and ethyl lactate; ethers such as tetrahydrofuran, 1,4-dioxane and ethylene glycol dimethyl ether; aliphatic hydrocarbons such as hexane, heptane, octane and cyclohexane; aromatic hydrocarbons such as toluene and xylene; nitriles such as acetonitrile, propionitrile and benzonitrile; and amides such as N,N-dimethylformamide, N,N-dimethylacetamide and N-methyl-2-pyrrolidone.

To allow the polymerization reaction to take place efficiently, it is desirable to use a polymerization initiator. Examples of the polymerization initiators include 2,2'-azobis(isobutyronitrile), 2,2'-azobis(2-methylbutyronitrile), 2,2'-azobis(2,4-dimethylvaleronitrile) (VA-065 manufactured by Wako Pure Chemical Industries, Ltd., 10-hour half-life temperature: 51° C.), 4,4'-azobis(4-cyanovaleric acid), 2,2'-azobis(4-methoxy-2,4-dimethylvaleronitrile), 1,1'-azobis(cyclohexane-1-carbonitrile), 1-[(1-cyano-1-methylethyl)azo]formamide, 2,2'-azobis[2-(2-imidazolin-2-yl)propane], 2,2'-azobis(2-methylpropionamidine) dihydrochloride, 2,2'-azobis[2-methyl-N-(2-hydroxyethyl) propionamide] (VA-086 manufactured by Wako Pure Chemical Industries, Ltd., 10-hour half-life temperature: 86° C.), benzoyl peroxide (BPO), 2,2'-azobis[N-(2-carboxyethyl)-2-methylpropionamidine] n-hydrate (VA-C57 manufactured by Wako Pure Chemical Industries, Ltd., 10-hour half-life temperature: 57° C.), 4,4'-azobis(4-cyanopentanoic acid) (V-501 manufactured by Wako Pure Chemical Industries, Ltd.), 2,2'-azobis[2-(2-imidazolin-2-yl)propane] dihydrochloride (VA-044 manufactured by Wako Pure Chemical Industries, Ltd., 10-hour half-life temperature: 44° C.), 2,2'-azobis[2-(2-imidazolin-2-yl)propane] disulfate dihydrate (VA-046B manufactured by Wako Pure Chemical Industries, Ltd., 10-hour half-life temperature: 46° C.), 2,2'-azobis[2-(2-imidazolin-2-yl)propane] (VA-061 manufactured by Wako Pure Chemical Industries, Ltd., 10-hour half-life temperature: 61° C.), 2,2'-azobis(2-amidinopropane) dihydrochloride (V-50 manufactured by Wako Pure Chemical Industries, Ltd., 10-hour half-life temperature: 56° C.), peroxodisulfuric acid and t-butyl hydroperoxide.

In consideration of water solubility, ion balance and interaction with the monomers, the solvent is preferably selected from 2,2'-azobis[2-methyl-N-(2-hydroxyethyl) propionamide], 2,2'-azobis[N-(2-carboxyethyl)-2-methylpropionamidine] n-hydrate, 4,4'-azobis(4-cyanopentanoic acid), 2,2'-azobis[2-(2-imidazolin-2-yl)propane] dihydrochloride, 2,2'-azobis[2-(2-imidazolin-2-yl)propane] disulfate dihydrate, 2,2'-azobis[2-(2-imidazolin-2-yl)propane], 2,2'-azobis(2-amidinopropane) dihydrochloride and peroxodisulfuric acid.

In consideration of solubility in organic solvents, ion balance and interaction with the monomers, it is preferable to use 2,2'-azobis(2,4-dimethylvaleronitrile) or 2,2'-azobis(isobutyronitrile).

The polymerization initiator may be added in an amount of 0.05 mass % to 10 mass % relative to the total mass of the monomers used in the polymerization.

The temperature may be raised to increase the solubility of the monomers and the polymer. For example, the reaction vessel may be heated at 50° C. to 200° C. in an oil bath or the like, and stirring may be performed for 1 hour to 48 hours. More preferably, the reaction vessel may be heated at 80° C. to 150° C., and stirring may be performed for 5 hours to 30 hours. These reaction conditions allow the polymerization reaction to proceed, resulting in a copolymer of the present invention. The reaction atmosphere is preferably a nitrogen atmosphere.

The reaction may be performed in such a manner that all the reaction materials are added to the reaction solvent at room temperature and are thereafter polymerized at an elevated temperature in the above-described range, or a mixture of the reaction materials is added all at once or added dropwise in small portions to the solvent that has been heated.

The molecular weight of the polymer (P5) may be about several thousands to several millions, and is preferably 5,000 to 5,000,000, more preferably 5,000 to 2,000,000, and still more preferably 5,000 to 1,000,000. The polymer may be a random copolymer, a block copolymer or a graft copolymer. The copolymerization reaction for producing the copolymer is not particularly limited, and may be any known synthesis method performed in a solvent such as radical polymerization, ion polymerization, photopolymerization, or polymerization using emulsion polymerization. Depending on the target purpose of use, the polymer (P5) of the present invention may be used as a single polymer or a mixture of a plurality of polymers (P5) in any ratio.

A composition used to form a coating of the polymer (P5) on at least a portion of the surface of the substrate may be prepared by diluting as required the polymer (P5) containing structural units of the formulae (1a) and (1c) and optionally of the formula (1d) to a predetermined concentration with an appropriate solvent. That is, the present invention provides a composition containing the polymer (P5) and a solvent.

The solvent may be water, an organic solvent, or a mixture of such solvents. The solvent may be selected appropriately in accordance with the type and properties of the polymer (P5). Examples include water; ketones such as acetone, methyl ethyl ketone, methyl isobutyl ketone, methyl isoamyl ketone, methyl amyl ketone and cyclohexanone; alcohols such as methanol, ethanol, isopropanol, ethylene glycol monomethyl ether, ethylene glycol monoethyl ether, propylene glycol monomethyl ether and propylene glycol monoethyl ether; esters such as methyl acetate, ethyl acetate, propyl acetate, isopropyl acetate, butyl acetate, methyl propionate, methyl lactate and ethyl lactate; ethers such as tetrahydrofuran, 1,4-dioxane and ethylene glycol dimethyl ether; aliphatic hydrocarbons such as hexane, heptane, octane and cyclohexane;

aromatic hydrocarbons such as toluene and xylene; nitriles such as acetonitrile, propionitrile and benzonitrile; and amides such as N,N-dimethylformamide, N,N-dimethylacetamide and N-methyl-2-pyrrolidone. The solvents may be used singly, or a mixture of solvents may be used.

The composition may be prepared from a varnish containing the polymer (P5). For example, the polymer (P5)-containing varnish may be prepared by a production method comprising a step in which a monomer capable of giving structural units of the formula (1a), a monomer capable of giving structural units of the formula (1c) and optionally an additional monomer are reacted (polymerized) in a solvent in a total monomer concentration of 0.01 mass % to 20 mass %. The polymer (P5) is preferably obtained by radical polymerization.

To form a coating uniformly, the solid concentration in the composition is preferably 0.01 to 50 mass %.

Where necessary, the composition may further contain other materials in addition to the polymer (P5) and the solvent without impairing the performance of a coating that is obtained. Examples of such additional materials include preservatives, surfactants, primers for enhancing the adhesion with the substrates, fungicides and sugars.

In an embodiment of the present invention, the substrate having a surface at least partially coated with the polymer (P4) or (P5) may be produced by applying the polymer (P4) or (P5) to a substrate. The polymer (P4) or (P5) may be applied to a substrate by any technique without limitation, and known techniques may be used appropriately. The term "apply" comprehends various actions such as to soak the substrate into the polymer or a polymer solution, and to cast the polymer or a polymer solution over the substrate and allow the substrate to stand for a predetermined time. The substrate may be soaked or allowed to stand for an appropriate amount of time at an appropriate temperature which are selected in accordance with the material of the substrate and the kind of the polymer. For example, these treatments may be performed at 10 to 35° C., preferably ambient temperatures (for example, 25° C.), for 30 seconds to 24 hours, preferably 1 minute to 3 hours. In the manner described above, the surface of the substrate is coated at least partially, preferably over the entirety thereof, with the polymer (P4) or (P5).

In an embodiment of the present invention, the substrate may be typically a dish, a plate, a porous membrane, particles or a filter. In particular, the substrate may be a dish, a plate, a porous membrane, particles or a filter each used for cell separation and/or cell culturing in experimental equipment, analytical equipment or medical equipment.

Examples of the materials of the substrates include glass, metals, metal-containing compounds or metalloid-containing compounds, activated carbons and resins. Examples of the metals include typical metals: (alkali metals: Li, Na, K, Rb, Cs; alkaline earth metals: Ca, Sr, Ba, Ra), magnesium group elements: Be, Mg, Zn, Cd, Hg; aluminum group elements: Al, Ga, In; rare earth elements: Y, La, Ce, Pr, Nd, Sm, Eu; tin group elements: Ti, Zr, Sn, Hf, Pb, Th; iron group elements: Fe, Co, Ni; earth-acid elements: V, Nb, Ta; chromium group elements: Cr, Mo, W, U; manganese group elements: Mn, Re; noble metals: Cu, Ag, Au; and platinum group elements: Ru, Rh, Pd, Os, Ir, Pt. Examples of the metal-containing compounds or the metalloid-containing compounds include inorganic solid materials including ceramics which are basically metal oxides in the solid form sintered by heat treatment at a high temperature, semiconductors such as silicon, and shaped products of inorganic compounds such as metal oxides or metalloid oxides (for example, silicon oxide and alumina), metal carbides or metalloid carbides, metal nitrides or metalloid nitrides (for example, silicon nitride), and metal borides or metalloid borides, aluminum, nickel-titanium, and stainless steel (for example, SUS304, SUS316 and SUS316L).

The resins as the substrate materials may be natural resins or derivatives thereof; or synthetic resins. Some preferred natural resins and derivatives thereof are cellulose, cellulose triacetate (CTA), nitrocellulose (NC) and dextran sulfate immobilized celluloses. Some preferred synthetic resins are polyacrylonitrile (PAN), polyester-based polymer alloy (PEPA), polystyrene (PS), polysulfone (PSF), polyethylene terephthalate (PET), polymethyl methacrylate (PMMA), polyvinyl alcohol (PVA), polyurethane (PU), ethylene vinyl alcohol (EVAL), polyethylene (PE), polyester, polypropylene (PP), polyvinylidene fluoride (PVDF), polyethersulfone (PES), polycarbonate (PC), polyvinyl chloride (PVC), polytetrafluoroethylene (PTFE), ultrahigh molecular weight polyethylene (UHPE), polydimethylsiloxane (PDMS), acrylonitrile-butadiene-styrene resin (ABS), Teflon (registered trademark), nylon, polymethylpentene (PMP) and various ion exchange resins.

In the substrate, the surface which is coated with the coating film may be composed of a single material or a combination of two or more materials. Of the materials mentioned above, glass, silicon, silicon oxide, polystyrene (PS), polypropylene (PP), Teflon (registered trademark), cycloolefin polymer (COP), polydimethylsiloxane (PDMS) or stainless steel (such as SUS304, SUS316 or SUS316L), or a combination of materials selected from above is preferable. The polymers of the present invention can form coatings under low drying temperature conditions, and are thus applicable even to resins or the like which are less heat resistant.

The above substrate is used directly, or is used after being washed with water or an appropriate medium, or after being subjected to surface treatment such as plasma treatment.

The present invention also provides a method for producing a ligand-bearing substrate which comprises a step of bringing a ligand containing a carbon-carbon triple bond or an azide group into contact with a substrate having a surface at least partially coated with the polymer (P4) or (P5). The method may comprise a step of applying a composition containing the polymer (P5) onto a desired substrate to produce a polymer (P5)-coated substrate, and a step of bringing a ligand containing an azide group or a carbon-carbon triple bond into contact with the polymer (P5)-coated substrate to cause the ligand to react with the corresponding carbon-carbon triple bond or azide group represented by Z in the polymer (P5).

In an embodiment of the present invention, the ligand may be introduced into the polymer (P4) or (P5) by a click reaction based on azide-alkyne cycloaddition reaction in which (i) structural units containing a carbon-carbon triple bond are brought into contact with a ligand containing an azide group, or (ii) structural units containing an azide group are brought into contact with a ligand containing a carbon-carbon triple bond. The click reaction may be performed on the polymer applied to a substrate. In the above embodiment, the ligand is preferably introduced in the manner (i).

The ligand containing a carbon-carbon triple bond or an azide group may be purchased as a click chemistry reagent from reagent suppliers such as Funakoshi Co., Ltd. or Sigma-Aldrich, or may be prepared from reagents available from reagent suppliers by methods which are known to those skilled in the art. When the polymer (P4) or (P5) contains (i) structural units containing a carbon-carbon triple bond, a ligand containing an azide group is selected. When the polymer contains (ii) structural units containing an azide group, a ligand containing a carbon-carbon triple bond is selected. That is, either the structural units or the ligand has a carbon-carbon triple bond, and the other has an azide group, and the contact between them easily forms a structure represented by the following formula (2a) or (2b). The ligand may be thus introduced into the polymer.

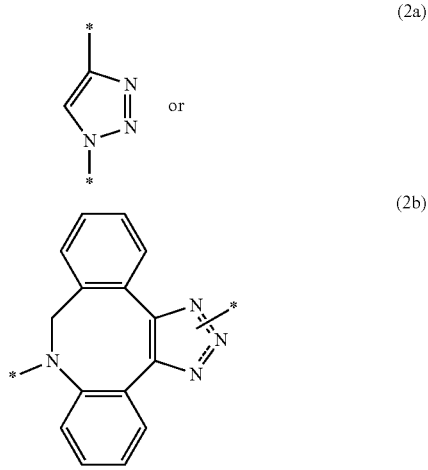

In an embodiment of the present invention, the case (i) is preferable.

The solvent which may be used in the click reaction is not particularly limited. Examples include aromatic hydrocarbons such as benzene, toluene and xylene; esters such as ethyl acetate and butyl acetate; ketones such as acetone and methyl ethyl ketone; amides such as N,N-dimethylformamide, N,N-dimethylacetamide and N-methyl-2-pyrrolidone; nitriles such as acetonitrile and propionitrile; ethers such as tetrahydrofuran and dioxane; C1-C4 alcohols such as methanol and ethanol; dimethyl sulfoxide; and water.

The click reaction may be carried out in the presence or absence of a copper catalyst. Examples of the copper catalysts which may be used in the click reaction include copper (I) bromide, copper (I) iodide, copper (II) acetate, copper (II) sulfate, and hydrates thereof. Typical examples of the reductants include ascorbic acid and salts thereof.

Where necessary, the click reaction may be performed in the presence of a nitrogen-containing ligand. The nitrogen-containing ligand enhances the efficiency of the cycloaddition catalyzed by a copper catalyst. Examples of such nitrogen-containing ligands include tris[(1-benzyl-1H-1,2,3-triazol-4-yl)methyl]amine and tris(2-benzimidazolylmethyl)amine.

Depending on the type of the click chemistry reagent, the reaction may be performed without adding a copper catalyst and a reductant. For example, a cyclooctyne derivative with a carbon-carbon triple bond represented by the formula (2b) described above has low activation energy due to the strain of the ring, and can easily react with azide even without a catalyst.

The ligand-bearing substrates obtained by the methods described hereinabove may be used after the completion of the click reaction, preferably after washing with water or a suitable medium.

EXAMPLES

Hereinbelow, the present invention will be described in greater detail by presenting Examples. However, it should be construed that the scope of the invention is not limited to such Examples.

Synthetic Example 1

Synthesis of Polymer Having Zwitterionic Group and Click Reaction Site 3.0 g of CMB (N-methacryloyloxyethyl-N,N-dimethylammonium-α-N-methylcarboxybetaine, manufactured by OSAKA ORGANIC CHEMICAL INDUSTRY LTD.), 4.0 g of PGMA (propargyl methacrylate) and 0.07 g of 2,2'-azobis[N-(2-carboxyethyl)-2-methylpropionamidine] hydrate (VA-C57 manufactured by Wako Pure Chemical Industries, Ltd.) were dissolved into 28.4 g of ethyl lactate. In a nitrogen atmosphere, the solution was stirred while performing heating at 80° C. overnight. Thereafter, ethanol was added to the reaction liquid to precipitate a polymer, which was then recovered and was dried under reduced pressure. Thus, a polymer having a structure represented by the following formula (1) was obtained. The weight average molecular weight of the polymer obtained was 8000 relative to standard polyethylene oxide and polyethylene glycol.

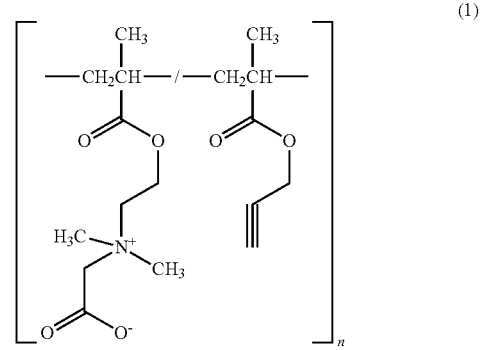

Synthetic Example 2

Synthesis of Polymers Having Zwitterionic Group, Click Reaction Site and Silane-Coupling Group Ternary copolymers poly(CMB-PGMA-MPTMS) were synthesized using methacryloyloxypropyltrimethoxysilane (MPTMS) capable of modifying glass or metal surface by chemical bonding. When the MPTMS composition ratio is 10 mol %, the highest coverage ratio is obtained and the adsorption and adhesion of proteins and cells can be controlled by CMB (J. Biomed. Mater. Res. A, 2016, 104A, 2029-2036). Based on this fact, the ternary copolymers were synthesized while using 10 mol % MPTMS and controlling the CMB:PGMA composition ratio to 80:10, 70:20 and 60:30. 45 mmol CMB and PGMA in total, 0.5 mmol MPTMS and 0.17 mmol AIBN were dissolved into ethanolklimethylformamide (3:1) mixed solvent. The reaction was performed in a nitrogen atmosphere at 70° C. for 4 hours. Thereafter, 0.034 mmol AIBN was added, and the reaction was further performed for 4 hours. Thus, a polymer having a structure represented by the following formula (2) was obtained.

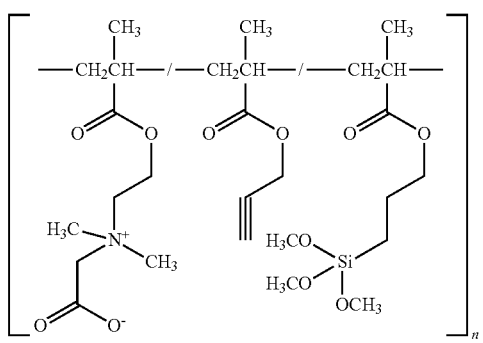

(2)

Synthetic Example 3

Synthesis of Peptides

The peptides described in Table 1 were synthesized by Fmoc solid-phase method. Peptide chains were elongated on Fmoc-Gly-Alko-PEG resin (N-α-(9-fluorenylmethoxycarbonyl)-glycine p-methoxybenzyl alcohol polyethyleneglycol resin, manufactured by WATANABE CHEMICAL INDUSTRIES, LTD.) as a support. The 7-9th Gly residues counted from the N terminus were introduced as a flexible linker. Azidohomoalanine (AHA) was introduced at the C terminus to make sure that the peptide could be finally introduced into the polymer chains by a click reaction. In peptides 2 and 3, the length of the flexible linker was changed. The peptide chains elongated on the resin were cleaved from the resin and deprotected to give crude peptides, which were then purified by reversed-phase high-performance liquid chromatography. The purified peptides were analyzed by MALDI TOF-MS to determine the molecular weight and were thereby identified.

TABLE 1

| Peptide names | Amino acid sequence |
|---|---|
| Peptide 1 (SEQ ID NO: 3) | Gln-Gln-Gly-Trp-Phe-Pro-Gly-Gly-Gly-AHA-Gly |
| Peptide 2 (SEQ ID NO: 4) | Gln-Gln-Gly-Trp-Phe-Pro-(Gly-Ala)$_7$-AHA-Gly |
| Peptide 3 (SEQ ID NO: 5) | Gln-Gln-Gly-Trp-Phe-Pro-AHA-Gly |

※AHA: Azidohomoalanine

The secondary structure of the oligopeptides shown in Table 1 was evaluated by circular dichroism (CD) spectroscopy. The spectra are illustrated in FIG. 1 (solid line: peptide 1, dotted line: peptide 2, long broken line: peptide 3). Peptide 1 had three Gly residues as a linker. It has been shown that the peptide structure is more random when a linker is introduced and when the length of the linker is longer, and the structure is β-strand when the sequence consists solely of Gln-Gln-Gly-Trp-Phe-Pro (SEQ ID NO: 1) which is a CD44-binding active site.

Example 1

Formation of Polymer Coating on Surface of Glass Plate

The polymer synthesized in Synthetic Example 1 was dissolved into ethyl lactate to give a 10% solution. Next, the solution was spin coated onto a 4×4 cm glass plate at 1115 rpm/60 s, and was heated on a hot plate at 100° C. for 1 minute. The glass plate was thereby coated with the polymer. The film thickness of the polymer was 500 nm.

Example 2

Introduction of Peptide 40 mg of peptide 1 synthesized in Synthetic Example 3 was suspended into 16 g of pure water. The suspension was mixed together with 0.43 g of 1 mg/ml aqueous copper sulfide solution and 2.7 g of 1 mg/ml aqueous sodium ascorbate solution to form a peptide reaction solution. The peptide reaction solution was dropped onto the entire surface of the glass plate fabricated in Example 1. The plate was allowed to stand as such at room temperature for 12 hours, and was thereafter washed with pure water and was air-blown. A peptide-bearing glass plate was thus fabricated.

Comparative Example 1

Application of Peptide to Polymer-Coated Glass Plate 40 mg of peptide 1 synthesized in Synthetic Example 3 was suspended into 16 g of pure water. The resultant peptide suspension was dropped onto the entire surface of the glass plate fabricated in Example 1. The plate was allowed to stand as such at room temperature for 12 hours, and was thereafter washed with pure water and was air-blown. A peptide-free glass plate was thus fabricated.

Example 3

Test of Confirming Presence of Supported Peptide

The plates fabricated in Example 2 and Comparative Example 1 were analyzed by Micro BCA method to examine the presence of supported peptide. This test was performed using BCA Protein Assay Reagent Kit manufactured by Thermo Fisher Scientific Inc. After the reagents were mixed, the plates fabricated in Example 2 and Comparative Example 1 were soaked into the respective reagent mixtures and were held at 60° C. for 1 hour. The solutions were recovered and were analyzed to measure the transmittance at 562 nm. The solution treated with the plate from Example 2 showed a transmittance of 32%, and the absorption by peptide bonds was confirmed. On the other hand, the solution treated with the plate from Comparative Example 1 had a transmittance of 80%. These results confirmed that the plate fabricated in Example 2 was a peptide-carrying-polymer-coated glass plate in which the peptide had been supported as a result of click reaction, and the plate fabricated in Comparative Example 1 was a peptide-free-polymer-coated glass plate.

Example 4

Cell Selectivity Evaluation

Figure 2:
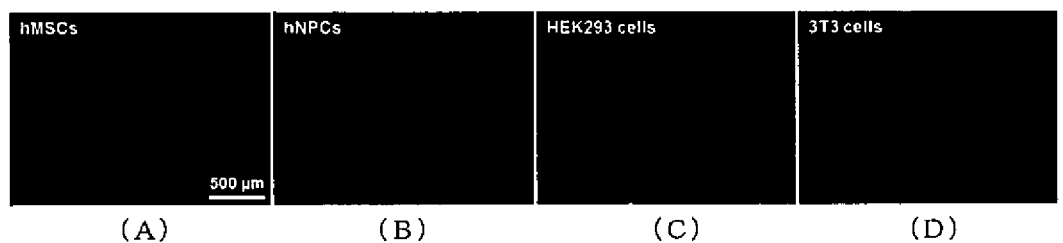
FIG. 2 is a set of optical micrographs of peptide-free-polymer-coated glass plates of Example 1 tested by the cell selectivity evaluation in Example 4. (A) is the result obtained using human bone marrow mesenchymal stem cells (hMSC); (B) the result obtained using human embryonic stem cell-derived neural precursor cells (hNPC); (C) the result obtained using human embryonic kidney-derived cells (HEK293 cells); and (D) the result obtained using mouse fibroblastic cells (3T3 cells).
Figure 3:
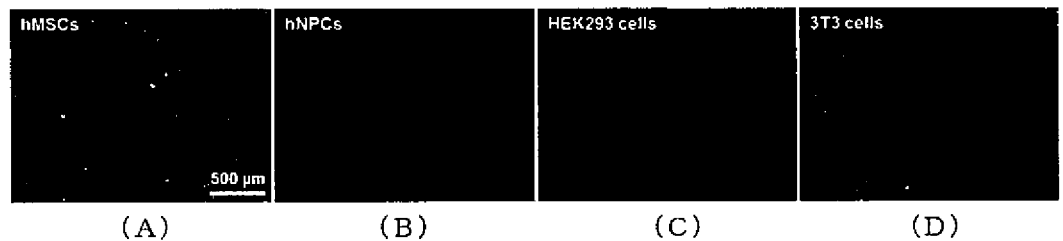
FIG. 3 is a set of optical micrographs of peptide-carrying-polymer-coated glass plates of Example 2 tested by the cell selectivity evaluation in Example 4. (A) is the result obtained using human bone marrow mesenchymal stem cells (hMSC); (B) the result obtained using human embryonic stem cell-derived neural precursor cells (hNPC); (C) the result obtained using human embryonic kidney-derived cells (HEK293 cells); and (D) the result obtained using mouse fibroblastic cells (3T3 cells).
Figure 4:
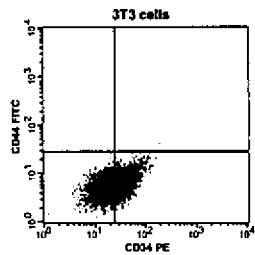
FIG. 4 shows the results of the flow cytometry of the peptide-carrying-polymer-coated glass plate of Example 2, tested by the cell (3T3 cell) selectivity evaluation in Example 4.

Studies were made to examine the capturing of human bone marrow mesenchymal stem cells (hMSC) to the surface of the peptide-carrying (Example 2)/peptide-free (Example 1) polymer-coated glass plates. Further, cell selectivity was evaluated using human embryonic stem cell-derived neural precursor cells (hNPC) and human embryonic kidney-derived cells (HEK293 cells), and mouse fibroblastic cells (3T3 cells). The peptide-bearing/peptide-free-polymer-coated glass plates were sterilized by being soaked into 70% ethanol solution and being dried in a clean bench. The culture fluids described in Table 2 below which were suited for the respective cells were provided. The states of cell adhesion 6 hours after cell seeding were observed. The results of Example 1 are shown in FIG. 2 (optical microscopic observation), and the results of Example 2 are shown in FIG. 3 (optical microscopic observation) and FIG. 4 (flow cytometry).

TABLE 2

| Cell types | Culture fluid composition |
|---|---|
| hMSC | DMEM supplemented containing 100 unit/mL penicillin and 100 μg/mL streptomycin with 10% fetal bovine serum |
| hNPC | DMEM/F12 containing 3 μM L-Glutamine, 5 mg/ml heparin, 100 U/ml penicillin and 100 mg/ml streptomycin supplemented with 2% (v/v) B27 supplement, 1% (v/v) N2 supplement, 20 ng/ml bFGF and 20 ng/ml EGF |
| HEK293 cell | DMEM supplemented containing 100 unit/mL penicillin and 100 μg/mL streptomycin with 10% fetal bovine serum |
| 3T3 cell | MEM supplemented containing 100 unit/mL penicillin and 100 μg/mL streptomycin with 10% fetal bovine serum |

Example 5

Evaluation of Cell Capture Rates, Cell Counts and Captured Cell Purity

Figure 5:
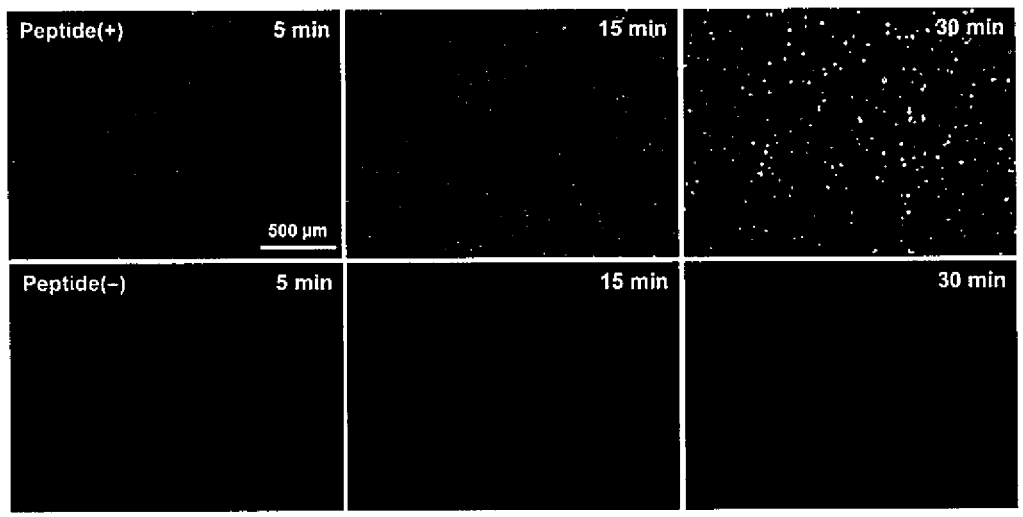
FIG. 5 is a set of optical micrographs of the surface of the peptide-carrying-polymer-coated glass plate (Example 2) and the surface of the peptide-free-polymer-coated glass plate (Example 1), tested by the cell (hMSC) capture rate evaluation in Example 5. The optical micrographs, from top left, show the results of cell seeding on the surface of the peptide-carrying-polymer-coated glass plate (Example 2) followed by incubation for 5 minutes, 15 minutes and 30 minutes, respectively. The optical micrographs, from bottom left, show the results of cell seeding on the surface of the peptide-free-polymer-coated glass plate (Example 1) followed by incubation for 5 minutes, 15 minutes and 30 minutes, respectively.
Figure 6:
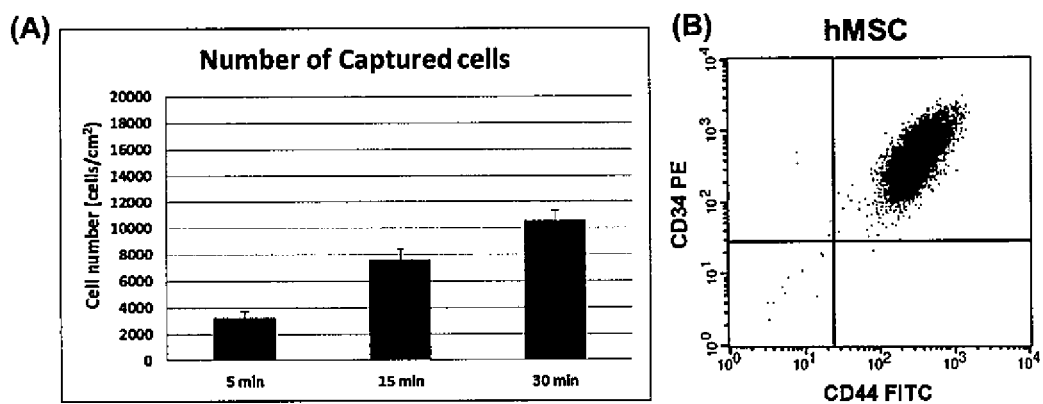
FIG. 6 shows the results of the peptide-carrying-polymer-coated glass plate (Example 2) tested by the cell (hMSC)

Cells were captured to the surface of the peptide-carrying-polymer-coated glass plate (Example 2) and the surface of the peptide-free-polymer-coated glass plate (Example 1), and the amounts of time required for the cell capturing, the cell counts, and whether the captured cells were hMSC were examined. First, hMSC alone was seeded in $3.0 \times 10^4$ cells/cm$^2$ and was incubated for 5, 15 or 30 minutes. The plates were then washed with the culture fluid, and the numbers of adhered cells were counted. The results are shown in FIG. 5 (optical microscopic observation) and FIG. 6(A) (cell counts). Further, the phenotypes of the captured cells were examined by flow cytometry, the results being shown in FIG. 6(B).

Figure 7:
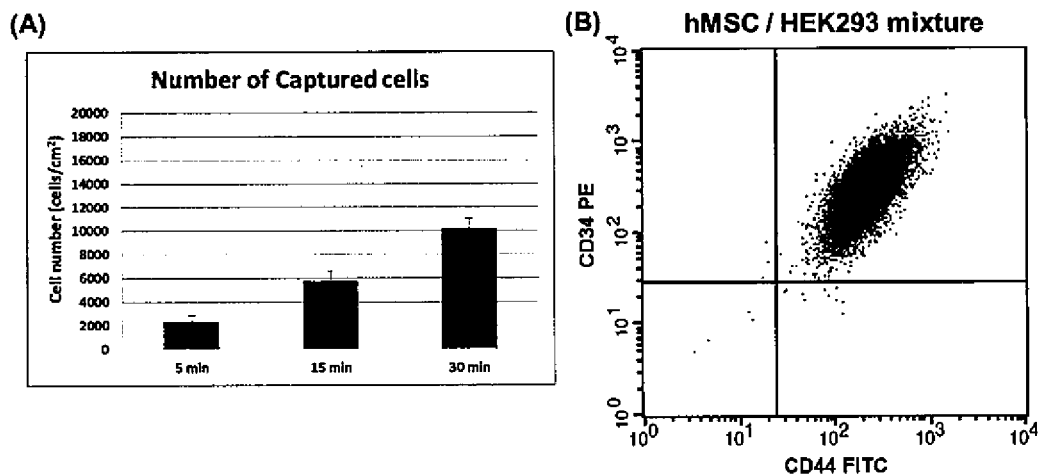
FIG. 7 shows the results of the peptide-carrying-polymer-coated glass plate (Example 2) tested by the evaluation of the rate of capture of hMSC from hMSC-HEK293 cell mixture in Example 5.

Subsequently, hMSC and HEK293 cells were mixed (each $1.5 \times 10^4$ cells/cm$^2$). The mixture was seeded and incubated for the predetermined amounts of time described above. The plates were then washed with the culture fluid, and the adhered cells were recovered and were studied to determine the cell counts and the phenotypes by flow cytometry. The results are shown in FIGS. 7(A) and 7(B), respectively.

As shown in FIG. 2, all the cell types, hMSCs, hNPCs, HEK293 cells and 3T3 cells, did not adhere to the glass plates coated with the polymer from Example 1 (the peptide-free-polymer-coated glass plates) in the evaluation of Example 4. This result confirmed that the base polymer synthesized in Synthetic Example 1 was non-cell adhesive.

As shown in FIG. 3, hMSCs adhered and spread on the peptide-carrying-polymer-coated glass plate from Example 2 in the evaluation of Example 4 (FIG. 3(A)), while hNPC (FIG. 3(B)) and HEK293 cells (FIG. 3(C)) did not adhere thereto. 3T3 cells showed adhesion, although weakly. Flow cytometry to evaluate the surface antigen expression showed that CD34-PE antibody had slightly bound to the surface (FIG. 4), suggesting a possibility of interaction with peptides. Based on the above results, it is clear that the material can selectively capture cells expressing CD34 on the surface.

As shown in FIG. 5, the adhered cell counts on the surface of the peptide-carrying-polymer-coated glass plates (Example 2) tended to increase with time in the evaluation of Example 5. On the other hand, there was no cell adhesion on the surface of the peptide-free-polymer-coated glass plates (Example 1). The numbers of hMSCs captured on the peptide-bearing surface were evaluated (FIG. 6(A)), and the results showed that approximately 40% of the seeded cells were captured. The surface antigen expression on the captured cells was evaluated by flow cytometry (FIG. 6(B)), and the results showed that the cells were positive for CD34 and also for CD44 (hMSC surface marker protein).

Further, the results of cell capture experiment with respect to the equivalent amount mixture of hMSC and HEK293 cells (FIG. 7(A)) showed that approximately 10000 cells/cm$^2$ had been trapped in 30 minutes of incubation. The surface antigen of the trapped cells was evaluated. The results (FIG. 7(B)) showed that almost all of the cells were both CD34 positive and CD44 positive, namely, were hMSC. Based on the above results, it is clear that the surface of the peptide-carrying-polymer-coated glass plate can selectively capture hMSC alone from hMSC-HEK293 cell mixture fluid.

Example 6

Modification of Glass Plates with Poly(CMB-PGMA-MPTMS) Ternary Copolymers

A glass plate was cleaned by strong acid treatment (such as piranha water or concentrated sulfuric acid), oxygen plasma treatment or UV/O$_3$ treatment, and was thereafter soaked into a 1 w/v % ethanol solution of poly(CMB-PGMA-MPTMS) synthesized in Synthetic Example 2. The glass plate was removed from the solution, washed with ethanol, and dried with N$_2$ gas. Thus, poly(CMB-PGMA-MPTMS)-modified glass plates were obtained.

Example 7

Introduction of Peptide

Peptide 1 was introduced onto the substrate-modifier polymers in the same manner as in Example 2.

Example 8

Wettability of Surface of Peptide-Carrying-Polymer-Modified Gglass Plates

Figure 8:
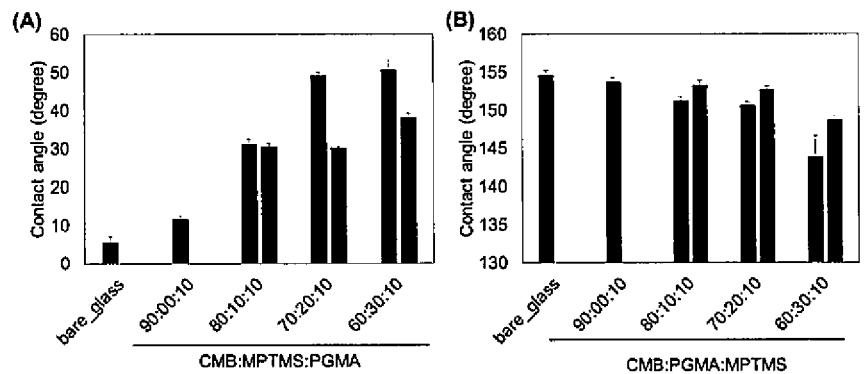
FIG. 8 is a set of graphs showing the results of water (droplet) contact angle measurement (A) and bubble contact angle measurement (B) in Example 8 to evaluate the wettability of the peptide-free-polymer-modified surfaces obtained in Example 6 and the peptide 1-carrying-polymer-modified surfaces obtained in Example 7. The results of the former surfaces are shown by black bars, and the results of the latter surfaces by gray bars.

The peptide-free- and peptide-carrying-polymer-modified surfaces obtained in Examples 6 and 7 were tested to evaluate wettability by water (droplet) contact angle measurement and bubble contact angle measurement. The results of the measurements are shown in FIGS. 8(A) and (B), respectively. The peptide-free-polymer-modified surfaces showed a larger droplet contact angle and a smaller bubble contact angle with increasing PGMA composition ratio (with decreasing CMB composition ratio), and were thus demonstrated to become less hydrophilic (the black bars in FIGS. 8(A) and 8(B)). These results are probably ascribed to the hydrophobicity of alkyne substituents min PGMA. On the other hand, the peptide-carrying-polymer-modified surfaces showed a small droplet contact angle and a large bubble contact angle as compared to the peptide-free surfaces (the gray bars in FIGS. 8(A) and 8(B)). These results may be understood as stemming from the surface hydrophilicity being increased by the introduction of hydrophilic peptide 1.

Example 9

Figure 9:
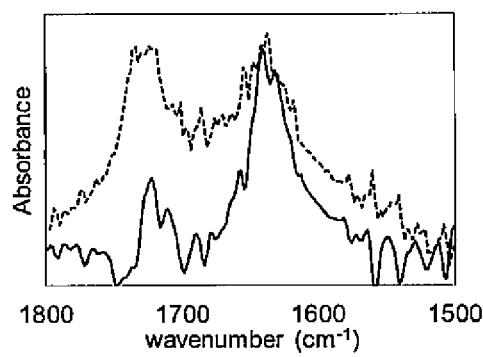
FIG. 9 shows spectra obtained by total reflection infrared spectrometry in Example 9 with respect to the glass surface modified with the peptide-free polymer (CMB:PGMA:MPTMS composition ratio=70:20:10) obtained in Example 6 and the glass surface modified with the peptide 1-carrying polymer (CMB:PGMA:MPTMS composition ratio=70:20:10) obtained in Example 7. The spectrum of the former surface is shown by a solid line, and the spectrum of the latter surface by a dotted line.

Evaluation of Introduction of Peptide 1 on Polymer-Modified Surface by Total Reflection Infrared Spectrometry The peptide-free- and peptide-carrying-polymer-modified surfaces obtained in Examples 6 and 7 were analyzed by total reflection infrared spectrometry. In the measurement, the polymer having a CMB:PGMA:MPTMS composition ratio of 70:20:10 was evaluated as the representative polymer. The results are shown in FIG. 9. In the amide II region (1700 to 1760 $cm^{-1}$) assigned to the amide bonds in peptide 1, the infrared absorbance of the peptide-carrying-polymer-modified surface (FIG. 9: dotted line) was significantly higher than the infrared absorbance of the peptide-free-polymer-modified surface (FIG. 9: solid line). The results will show that the polymer chains were modified by peptide 1 as a result of click reaction between the alkyne side chains of the base-modifying polymer and the azide groups of peptide 1.

Example 10

Evaluation of Film Thickness of Peptide 1-Carrying-Polymer-Modified Surfaces

Figure 10:
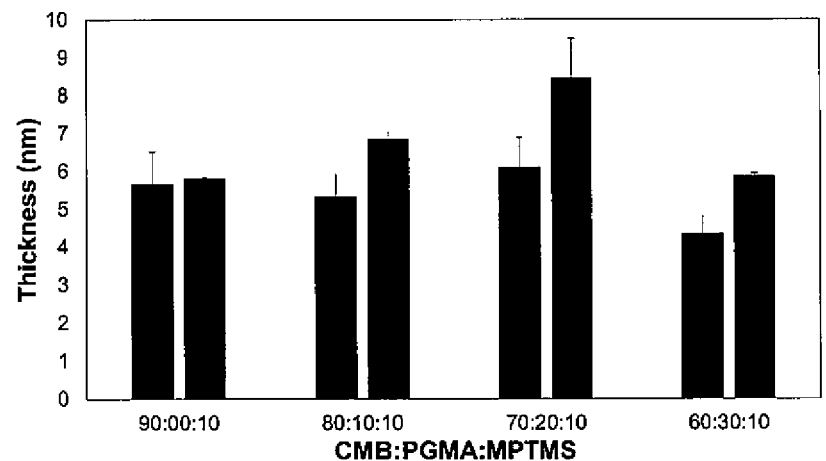
FIG. 10 is a graph showing the results of ellipsometry in Example 10 to measure the film thickness of the peptide-free-polymer-modified surfaces obtained in Example 6 and the peptide 1-carrying-polymer-modified surfaces obtained in Example 7. The results of the former surfaces are shown by black bars, and the results of the latter surfaces by gray bars.

The peptide-free- and peptide-carrying-polymer-modified surfaces obtained in Examples 6 and 7 were analyzed by ellipsometry measurement to determine the dry film thickness. The results are shown in FIG. 10. The film thicknesses of the peptide-free-polymer-modified surfaces were 4 to 6 nm (the black bars in FIG. 10), and the polymers of all compositions were shown to have formed thin films. The film thicknesses of the peptide 1-carrying-polymer-modified surfaces were 1 to 2.5 nm larger than the peptide-1-free surfaces (the gray bars in FIG. 10). In view of the fact that the film thicknesses before and after the peptide reaction were the same on the polymer-modified surfaces with CMB:PGMA:MPTMS=90:00:10, the increase in film thickness was probably brought about by the introduction of peptide 1.

Example 11

Quantitative Determination of Supported Peptide 1

Figure 11:
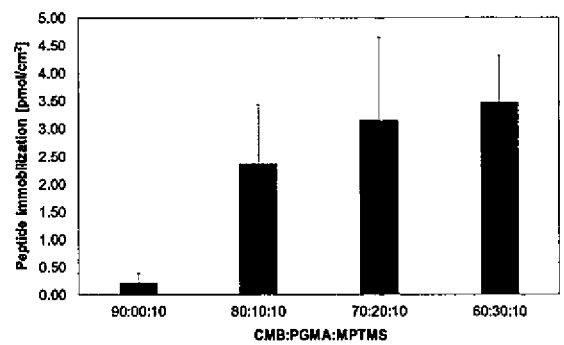
FIG. 11 is a graph showing the amounts of peptide 1 supported on the peptide-carrying-polymer-modified surfaces obtained in Example 7, determined by micro BCA assay in Example 11.

The peptide-carrying-polymer-modified surfaces obtained in Example 7 were analyzed by micro BCA method (n=3) to determine the amounts of peptide 1 supported on the surface. The results are shown in FIG. 11. The amount of supported peptide 1 tended to increase depending on the increase in PGMA composition ratio, namely, the introduction amount of alkyne side chains. The results also showed that the amount of supported peptide 1 could be changed from 2.5 pmol to 3.65 pmol per 1 $cm^2$ depending on the introduction amount of alkyne side chains.

From the evaluation results in the droplet/bubble contact angle measurements, the total reflection infrared spectrometry, the ellipsometry measurement and the quantitative determination of supported peptide 1 in Examples described above, it is clear that peptide 1 can be supported onto a modifier polymer applied to a base. It has been also found that the composition ratio of peptide 1 can be changed by manipulating the PGMA composition ratio.

Example 12

Figure 12:
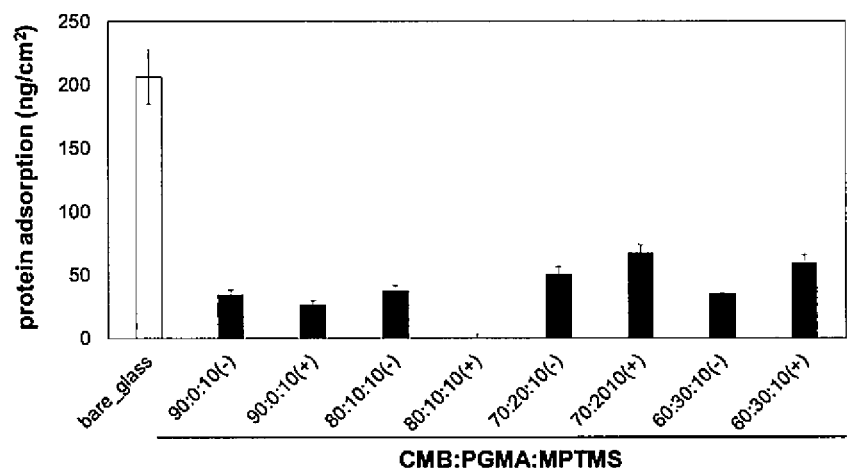
FIG. 12 is a graph showing the amounts of serum protein adsorption determined by micro BCA assay in Example 12 to evaluate the presence or absence of nonspecific protein adsorption to a glass plate, the peptide-free-polymer-modified surfaces obtained in Example 6 and the peptide 1-carrying-polymer-modified surfaces obtained in Example 7. The white bar shows the result of the glass plate, the black bars indicate the results of the peptide-free-polymer-modified surfaces, and the gray bars show the results of the peptide 1-carrying-polymer-modified surfaces.

Evaluation of Nonspecific Adsorption of Serum Protein to Peptide 1-Carrying-Polymer-Modified Surfaces To evaluate the presence or absence of nonspecific adsorption of protein to the peptide 1-carrying-polymer-modified surfaces obtained in Example 7, the amount of serum protein adsorption was determined by micro BCA method (n=3). The results are shown in FIG. 12. A glass plate was evaluated as control, and approximately 200 ng protein adsorbed per 1 $cm^2$ (the white bar in FIG. 12). In contrast, the peptide-free-polymer-modified surfaces obtained in Example 6 were shown to adsorb far less protein, with the amounts of protein adsorption being 30 to 50 ng/$cm^2$ (the black bars in FIG. 12). Similarly to the peptide-free-polymer-modified surfaces, the peptide 1-carrying-polymer-modified surfaces attained significant reduction in nonspecific adsorption of serum protein (the gray bars in FIG. 12). These results suggest that the introduction of peptide 1 does not inhibit the performance of CMB in controlling nonspecific protein adsorption, and that serum protein does not nonspecifically interact with supported peptide 1 or does not inhibit the specific interaction of peptide 1.

Based on the results, the following two points can be expected. (1) The nonspecific adhesion of cells can be controlled. (2) Specific cells can be exclusively captured through peptide 1. Selective cell capturing and selective cell culturing can be thus realized.

Example 13

Selective Capturing of Cells to Peptide 1-Carrying-Polymer-Modified Surfaces

Figure 13:
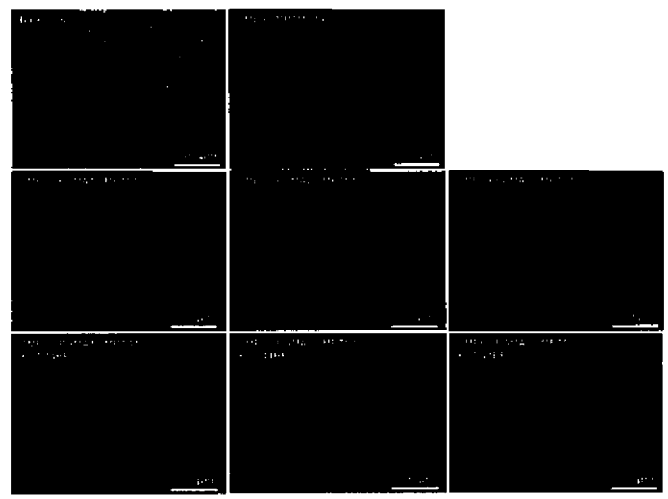
FIG. 13 is a set of phase-contrast micrographs after seeding of NIH3T3 cells onto peptide-free-polymer-modified surfaces and peptide 1 (CD44BP)-carrying-polymer-modified surfaces in Example 13.
Figure 14:
FIG. 14 is a set of phase-contrast micrographs after seeding of HEK293 cells onto peptide-free-polymer-modified surfaces and peptide 1 (CD44BP)-carrying-polymer-modified surfaces in Example 13.
Figure 15:
FIG. 15 is a set of phase-contrast micrographs after seeding of MSC onto peptide-free-polymer-modified surfaces and peptide 1 (CD44BP)-carrying-polymer-modified surfaces in Example 13.
Figure 16:
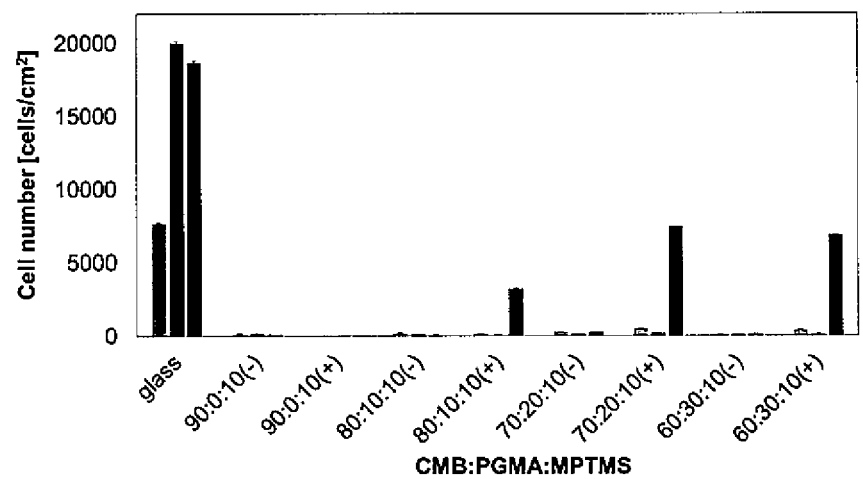
FIG. 16 is a graph showing the results of the determination of the counts of cells (n=3) captured on peptide-free-polymer-modified surfaces (−) and peptide 1-carrying-polymer-modified surfaces (+) in Example 13. The results of NIH3T3 cells are shown by light gray bars, the results of HEK293 cells by dark gray bars, and the results of human MSC by black bars.

Selective cell capturing to the peptide-free- and peptide-carrying-polymer-modified surfaces was evaluated. Three types of cells, NIH3T3 cells, HEK293 cells and human MSC, were seeded (each 3.0×$10^4$ cells/$cm^2$) onto the surfaces of the plates fabricated in Examples 6 and 7. After 12 hours of incubation, the captured cell counts and the cell spreading degrees were microscopically evaluated. The results are shown in FIGS. 13 to 16. FIGS. 13 to 15 are phase-contrast micrographs of the modified surfaces after seeding of the respective cells. FIG. 16 is a graph showing the results of the determination of the counts of cells (n=3) captured on the peptide-free-polymer-modified surfaces (−) and the peptide 1-carrying-polymer-modified surfaces (+). The results of NIH3T3 cells are shown by light gray bars, the results of HEK293 cells by dark gray bars, and the results of human MSC by black bars. The results show that no cells were captured or attached to the peptide-free-polymer-modified surfaces, and that the peptide 1-carrying-polymer-modified surfaces did not capture NIH3T3 cells or HEK293 cells, and did capture human MSC alone. It is probable that CD44 antigens were present on the surface of human MSC membranes, and human MSC alone was selectively captured and adhered as a result of peptide 1 capable of specifically interacting with CD44 (CD44-binding peptide, CD44BP) being supported on the polymer-modified surface.

It has been also found that more cells were captured with increasing composition ratio of PGMA, namely, with increasing amount of alkyne side chains. This result probably stems from the fact that an increased amount of alkyne side chains allowed an increased amount of peptide 1 to be supported. It can be thus said that the result is correlated to the results shown in Example 11. The number of captured human MSC was significantly reduced as compared to the adhered cell count on the glass plate. This result probably indicates that the polymers rejected cells expressing less CD44 antigens due to the progress of differentiation even to a small degree, and exclusively captured human MSC highly expressing CD44 antigens. Thus, the polymers successfully constructed a highly cell-selective surface on the base.

The invention claimed is:

1. A ligand-bearing substrate having a surface at least partially coated with a polymer (P3) comprising structural units represented by the following formulae (1a) and (1b):

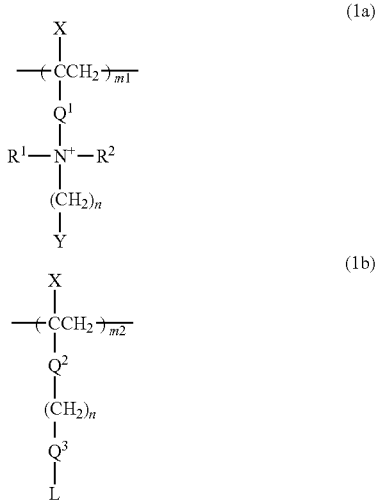

wherein $R^1$ and $R^2$ each independently denote a C1-C5 linear alkyl group, X denotes a hydrogen atom or a C1-C5 linear alkyl group, Y denotes a carboanion (—COO⁻ group) or a sulfoanion (—SO₃⁻ group), L denotes a ligand, $Q^1$ and $Q^2$ each independently denote an ester bond, an amide bond, a C1-C10 linear or branched alkylene group or an optionally substituted phenylene group, or a divalent group composed of a combination of any of the above bonds and groups, $Q^3$ denotes a divalent organic group containing a 1,2,3-triazole ring skeleton, m1 and m2 each independently denote an integer of 1 to 200, and n independently at each occurrence denotes an integer of 1 to 10.

2. The ligand-bearing substrate according to claim 1, wherein the ligand is selected from the group consisting of peptides, antibodies, proteins and low-molecular compounds.

3. The ligand-bearing substrate according to claim 2, wherein the peptide comprises Gln-Gln-Gly-Trp-Phe sequence.

4. The substrate according to claim 1, which is a cell separation substrate.

5. The substrate according to claim 1, which is a cell culture substrate.

6. The substrate according to claim 1, wherein the substrate is a dish, a plate, a porous film, a particle or a filter.

7. The substrate according to claim 4, which is capable of allowing at least one type of cells to be selectively separated from a cell mixture fluid containing at least two or more types of cells.

8. A cell separation method using the substrate described in claim 1.

9. The substrate according to claim 5, which is capable of allowing at least one type of cells to be selectively cultured from a cell mixture fluid containing at least two or more types of cells.

10. A cell culture method using the substrate described in claim 1.

11. The ligand-bearing substrate according to claim 1, wherein the polymer (P3) further comprises a structural unit represented by the following formula (1d):

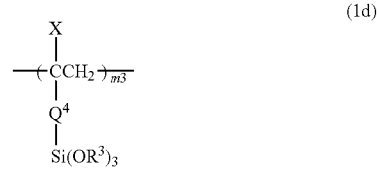

wherein $R^3$ independently at each occurrence denotes a C1-C5 linear alkyl group, X denotes a hydrogen atom or a C1-C5 linear alkyl group, $Q^4$ denotes an ester bond, a phosphodiester bond, an amide bond, a C1-C10 linear or branched alkylene group or an optionally substituted phenylene group, or a divalent group composed of a combination of any of the above bonds and groups, and m3 denotes an integer of 1 to 200.

* * * * *